United States Patent
Wilcox et al.

(10) Patent No.: US 9,220,749 B2
(45) Date of Patent: *Dec. 29, 2015

(54) METHOD OF INHIBITING CLOSTRIDIUM DIFFICILE BY ADMINISTRATION OF ORITAVANCIN

(71) Applicant: THE MEDICINES COMPANY, Parsippany, NJ (US)

(72) Inventors: Mark Harvey Wilcox, Leeds (GB); Simon Baines, Leeds (GB); Dario Lehoux, Terrebonne (CA); Thomas R. Parr, Indianapolis, IN (US)

(73) Assignee: THE MEDICINES COMPANY, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/101,645

(22) Filed: Dec. 10, 2013

(65) Prior Publication Data

US 2014/0100157 A1  Apr. 10, 2014

Related U.S. Application Data

(60) Continuation of application No. 13/950,202, filed on Jul. 24, 2013, now Pat. No. 8,629,100, which is a division of application No. 12/676,420, filed as application No. PCT/US2008/075949 on Sep. 11, 2008, now Pat. No. 8,518,873.

(60) Provisional application No. 60/971,766, filed on Sep. 12, 2007.

(51) Int. Cl.
| | |
|---|---|
| A61K 31/33 | (2006.01) |
| A61K 39/00 | (2006.01) |
| A61K 39/02 | (2006.01) |
| A61K 39/08 | (2006.01) |
| A61K 38/14 | (2006.01) |
| A01N 43/90 | (2006.01) |

(52) U.S. Cl.
CPC ............... *A61K 38/14* (2013.01); *A01N 43/90* (2013.01)

(58) Field of Classification Search
None
See application file for complete search history.

(56) References Cited

U.S. PATENT DOCUMENTS

| | | |
|---|---|---|
| 2004/0106590 A1 | 6/2004 | Eisenstein |
| 2005/0197333 A1 | 9/2005 | van Duzer et al. |
| 2006/0040871 A1* | 2/2006 | Levey et al. .................. 514/19 |
| 2007/0014849 A1 | 1/2007 | Jabes et al. |

FOREIGN PATENT DOCUMENTS

WO  WO 03/101488  * 12/2003  ............ A61K 45/00

OTHER PUBLICATIONS

McKay et al.; Journal of Antimicrobial Chemotherapy; Jun. 2009; 63(6):1191-9.*
Oritavancin Drug Facts Information (16 pages); revised Sep. 2014.*
Babakhani et al.; Journal of Medical Microbiology (2011), 60, 1213-1217.*
Methods for Determining Bactericidal Activity of Antimicrobial Agents: Approved Guideline; NCCLS; M26-A; vol. 19, No. 18; published Sep. 1999.*
Mercier et al.; Expert Rev. Anti Infect. Ther. 3(3), 325-332 (2005).*
Sillerstrom et al., In vitro Activity of LY 333328 Against Anaerobic Gram-Positive Bacteria. J. Chemotherapy 11 (2):90-92 (1999).
Van Bambeke, F., Glycopeptides and glycodepsipeptides in clinical development: A comparative review of their antibacterial spectrum, pharmacokinetics and clinical efficacy. Curr. Opin. Invest. Drugs 7(8):740-749 (2006).
Ward, K. et al., Oritavancin—an investigational glycopeptide antibiotic, Expert Opinion on Investigational Drugs, 2006, vol. 15, No. 4, pp. 417-429.
Baines, S. et al., Comparison of oritavancin versus vancomycin as treatments for clindamycin-induced Clostridium difficile PCR ribotype 027 infection in a human gut model, Journal of Antimicrobial Chemotherapy, 2008, vol. 62, No. 5, pp. 1078-1085.
Supplementary European Search Report dated Nov. 28, 2011, from the European Patent Office in corresponding European Application No. EP 08830916.6.
Mercier et al., Effect of growth phase and pH on the in vitro activity of a new glycopeptide, oritavancin (LY333328), against *Staphylococcus aureus* and *Enterococcus faecium*, Journal of Antimicrobial Chemotherapy (2002) 50, pp. 19-24.
Boylan et al., Pharmacodynamics of Oritavancin (LY333328) in a Neutropenic-Mouse Thigh Model of *Staphylococcus aureus* Infection, Antimicrobial Agents and Chemotherapy; May 2003; pp. 1700-1706.
Than, L., A new glycopeptide antimicrobial—oritavancin. Chinese J. New Drugs 16(14):1141-1144 (2007).
English translation of Office Action dated Mar. 15, 2013, issuing in Chinese counterpart application No. 200880110244.8.
Canadian Office Action issued Sep. 10, 2015 in corresponding Canadian Application No. 2,699,550.
Allen et al., "Mechanism of action of oritavancin and related glycopeptide antibiotics", *FEMS Microbiology Reviews*, 2003, No. 26, pp. 511-532.

* cited by examiner

*Primary Examiner* — Jeffrey T Palenik

(74) *Attorney, Agent, or Firm* — Wenderoth, Lind & Ponack, L.L.P.

(57) ABSTRACT

Glycopeptide antibiotics, such as oritavancin, demonstrate significant activity against both a vegetative form of *C. difficile* and *C. difficile* spores. Methods for the treatment, prophylaxis and prevention of *C. difficile* infection and disease in animals, including humans, are described.

13 Claims, 14 Drawing Sheets

Figure 6. Percentage isolation (+/-range) of Clostridium difficile spores following exposure to metronidazole (9.3mg/L), vancomycin (350mg/L), and oritavancin (350mg/L).

METHOD OF INHIBITING *CLOSTRIDIUM DIFFICILE* BY ADMINISTRATION OF ORITAVANCIN

CROSS-REFERENCE TO RELATED APPLICATIONS

The present application is a continuation of U.S. application Ser. No. 13/950,202, filed Jul. 24, 2013, which was a divisional of U.S. application Ser. No. 12/676,420, filed Aug. 23, 2010, now issued as U.S. Pat. No. 8,518,873, which was a U.S. national stage application under 35 U.S.C. §371 of international application number PCT/US08/075,949, filed Sep. 11, 2008, which claimed benefit of U.S. application No. 60/971,766, filed Sep. 12, 2007.

BACKGROUND OF THE INVENTION

*Clostridium difficile* infection is a major healthcare burden. It is a major cause of morbidity in the hospitalized elderly and is almost exclusively associated with antimicrobial therapy. *C. difficile* infection (CDI) may range in severity from mild antibiotic-associated diarrhea/colitis to life-threatening pseudomembranous colitis (Borriello, S. P. 1998. *J Antimicrob Chemother.* 41 (Suppl. C), 13-19). Treatment strategies for CDI have changed little over the past two decades: oral metronidazole (250-500 mg TID or QID) or vancomycin (125 mg QID) are most commonly used to treat CDI (Wilcox, M. H. 1998. *J Antimicrob Chemother.* 41 (Suppl. C), 41-46; see also the website postgradmed.com/issues/2002/11_02/joyce3.htm).

*C. difficile* sporulates to form bacterial spores that are resistant to extremes of heat, radiation, chemical assault, desiccation and time (Aronson, A. I, Fitz-James, P. 1976. *Bacteriol Rev.* 40, 360-402). *C. difficile* spores are known to survive in the nosocomial environment and are thought to play a role in transmission of the organism. Moreover, *C. difficile* spores are recalcitrant to antimicrobial therapy (including metronidazole (MET) and vancomycin (VAN) treatment) and may play a role in recurrent CDI following the cessation of the antibiotic used to treat an initial episode (Walters, B. A. 1983. *Gut.* 24, 206-212). However, few studies have evaluated antimicrobial activity against *C. difficile* spores, and the need for therapies that may be used to kill or block germination of *C. difficile* spores is great.

BRIEF SUMMARY OF THE INVENTION

As disclosed herein, it has been discovered that the glycopeptide antibiotic oritavancin, also known in the art and referred to herein as $N^{DISACC}$-(4-(4-chlorophenyl)benzyl) A82846B and LY333328, demonstrates significant activity against both a vegetative form of *C. difficile* and *C. difficile* spores. The results of the experiments described herein demonstrate that glycopeptide antibiotics, such as oritavancin (or its pharmaceutically acceptable salts, hydrates, or solvates thereof, or a mixture thereof), will be efficacious in the treatment, prophylaxis and/or prevention of disease caused by *C. difficile* in animals, including humans.

Inhibiting Growth of *C. difficile*

The invention is generally directed to methods of inhibiting the growth of *C. difficile* bacteria, in vitro, in vivo and/or ex vivo, comprising contacting *C. difficile* with a glycopeptide antibiotic in an amount sufficient to inhibit the growth of *C. difficile* bacteria. *C. difficile* may be in the form of a vegetative cell, a spore or a mixture of both. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is also directed to a method of inhibiting activation of a *C. difficile* spore, either in vitro, in vivo or both, comprising contacting a *C. difficile* spore with a glycopeptide antibiotic in an amount sufficient to inhibit activation of a *C. difficile* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is further directed to a method of inhibiting germination of a *C. difficile* spore, either in vitro, in vivo or both, comprising contacting a *C. difficile* spore with a glycopeptide antibiotic in an amount sufficient to inhibit germination of a *C. difficile* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is additionally directed to a method of inhibiting outgrowth of a *C. difficile* spore, either in vitro, in vivo or both, comprising contacting a *C. difficile* spore with a glycopeptide antibiotic in an amount sufficient to inhibit outgrowth of a *C. difficile* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

Moreover, the invention is directed to a method of inhibiting growth of a vegetative form of *C. difficile*, either in vitro, in vivo or both, comprising contacting a vegetative form of *C. difficile* with a glycopeptide antibiotic in an amount sufficient to inhibit a vegetative form of *C. difficile*. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is directed to a method of inhibiting *C. difficile* sporulation, either in vitro, in vivo or both, comprising contacting a vegetative form of *C. difficile* with a glycopeptide antibiotic in an amount sufficient to inhibit *C. difficile* sporulation. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

Treatment of *C. difficile* Infections

The invention is generally directed to methods of treating a *C. difficile* infection in a subject, comprising administering a therapeutically effective amount of a glycopeptide antibiotic to a subject having a *C. difficile* infection. Preferably, *C. difficile* is in the form of a vegetative cell, a spore or a mixture of both. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

The invention is also directed to a method of treating a *C. difficile* infection in a subject, comprising administering a therapeutically effective amount of a glycopeptide antibiotic to a subject having a *C. difficile* infection, wherein said treatment inhibits activation of a *C. difficile* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

The invention is further directed to a method of treating a *C. difficile* infection in a subject, comprising administering a therapeutically effective amount of a glycopeptide antibiotic to a subject having a *C. difficile* infection, wherein said treatment inhibits germination of a *C. difficile* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

The invention is additionally directed to a method of treating a *C. difficile* infection in a subject, comprising administering a therapeutically effective amount of a glycopeptide antibiotic to a subject having a *C. difficile* infection, wherein said treatment inhibits outgrowth of a *C. difficile* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

Moreover, the invention is directed to a method of treating a *C. difficile* infection in a subject, comprising administering a therapeutically effective amount of a glycopeptide antibiotic to a subject having a *C. difficile* infection, wherein said treatment inhibits growth of a vegetative form of *C. difficile*. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

Moreover, the invention is directed to a method of treating a *C. difficile* infection in a subject, comprising administering a therapeutically effective amount of a glycopeptide antibiotic to a subject having a *C. difficile* infection, wherein said treatment inhibits *C. difficile* sporulation. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

Prevention of *C. difficile* Infections

The invention is generally directed to methods of preventing a *C. difficile* infection in a subject, comprising administering to a subject at risk of *C. difficile* infection an amount of a glycopeptide antibiotic sufficient to prevent *C. difficile* infection. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

Prophylaxis of *C. difficile* Infections

The invention is generally directed to methods for providing prophylaxis of a *C. difficile* infection in a subject, comprising administering to a subject having a *C. difficile* infection an amount of a glycopeptide antibiotic sufficient to achieve prophylaxis of a *C. difficile* infection. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

The present invention includes a glycopeptide antibiotic, preferably oritavancin or pharmaceutically acceptable salt, hydrate, or solvate thereof, for use as a medical treatment in the treatment, prophylaxis and/or prevention of *C. difficile* infection in a subject.

The present invention also includes the use of a glycopeptide antibiotic in the manufacture of a medicament for treatment, prophylaxis and/or prevention of *C. difficile* infection in a subject. Preferably, said glycopeptide antibiotic is oritavancin, or pharmaceutically acceptable salt, hydrate, or solvate thereof, or a mixture thereof.

The present invention includes a kit comprising the pharmaceutical composition or a glycopeptide antibiotic of the present invention and written instructions for its use in treatment, prophylaxis and/or prevention of *C. difficile* infection, in a suitable container.

spores and vegetative cells (V) exposed to 10 mg/L oritavancin (ORI) vs no antimicrobial (C).

Figure 6:
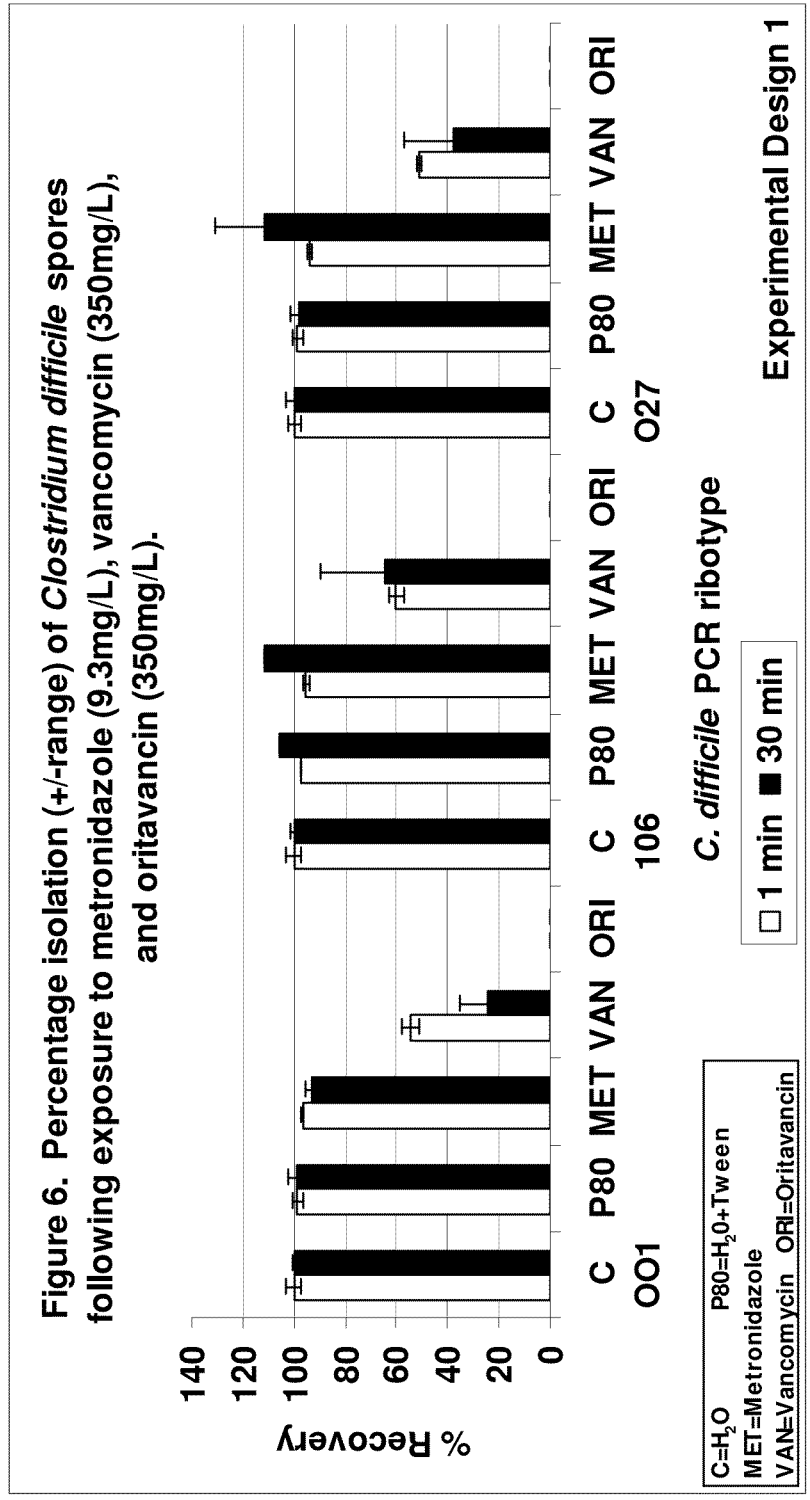

FIG. 6 shows the percentage of recovery of *C. difficile* spores exposed to metronidazole (MET), vancomycin (VAN) or oritavancin (ORI) for a very short period of time (1 min; light gray) or 30 minutes (30 min; dark gray), versus controls exposed to water alone (C) or water and Tween 80 (P80). Three strains of *C. difficile* spores were tested (PCR ribotypes 001, 106 and 027). Diluent was added to filtration cupules after addition of reaction solutions.

Figure 7:
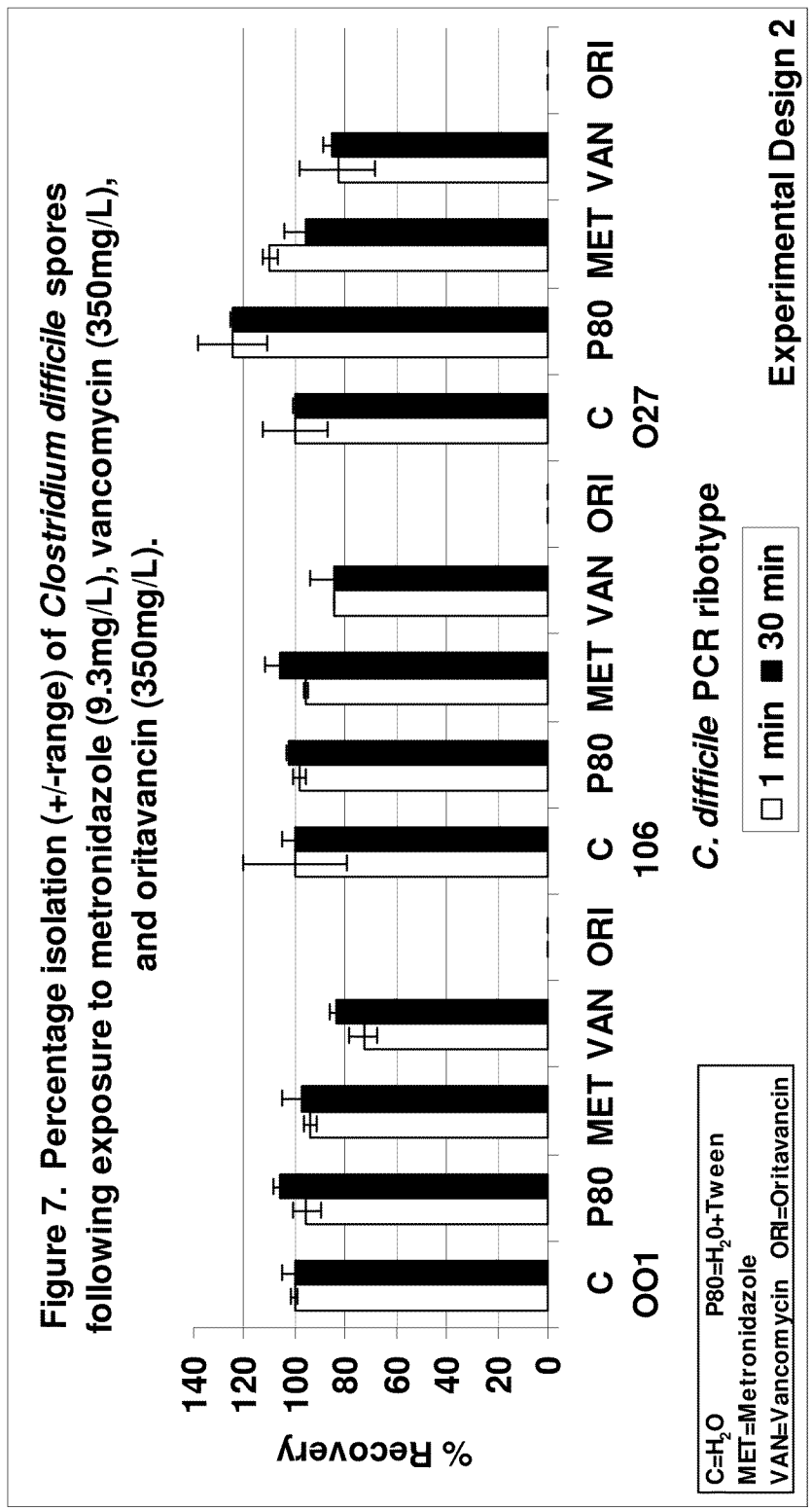

FIG. 7 shows the percentage of recovery of *C. difficile* spores exposed to metronidazole (MET), vancomycin (VAN) or oritavancin (ORI) for a very short period of time (1 min; light gray) or 30 minutes (30 min; dark gray), versus controls exposed to water alone (C) or water and Tween 80 (P80). Three strains of *C. difficile* spores were tested (PCR ribotypes 001, 106 and 027). Diluent was added to filtration cupules before addition of reaction solutions.

FIG. 8 shows the mean (+SE) viable counts ($\log_{10}$ cfu/mL) of culturable indigenous gut microflora in vessel 3 of (a) oritavancin and (b) vancomycin gut models. Vertical lines indicate the final day of each experimental period. Horizontal dashed lines indicate the limit of detection for bacterial culture.

FIG. 9 shows the mean (+SE) *C. difficile* PCR ribotype 027 total counts ($\log_{10}$ cfu/mL), spore counts ($\log_{10}$ cfu/mL), cytotoxin titres (RU) and antimicrobial concentrations (mg/L) in (a) oritavancin (ORI) and (b) vancomycin (VAN) experiments in vessel 3 of the gut model. Horizontal dashed lines indicate the limit of detection for bacterial culture.

Figure 10:
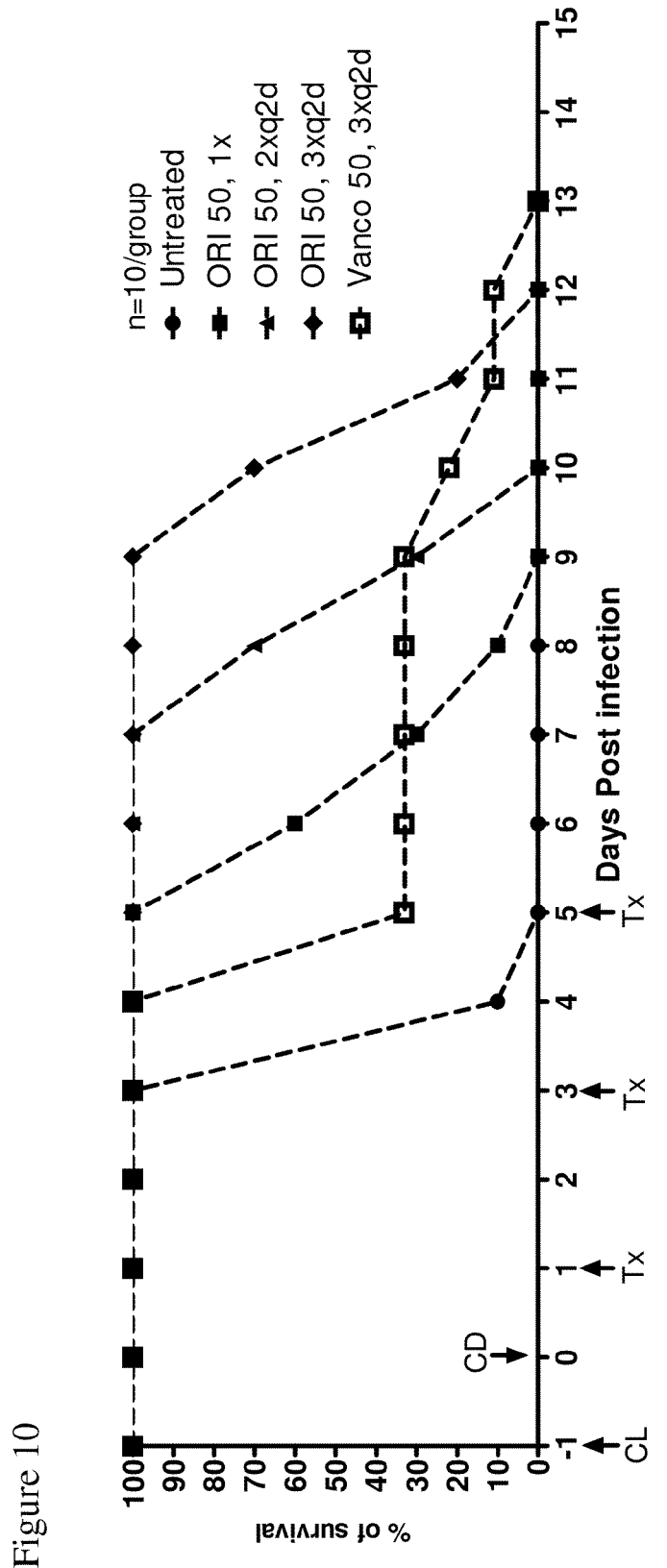

FIG. 10 shows the graphic results of a determination of the efficacy of multiple dose regimen of oritavancin compared to vancomycin in the hamster model of CDI. Hamsters (n=10/group) were treated intravenously with either oritavancin or vancomycin at different dose regimens. A total of 1, 2 or 3 doses of antibiotics were injected intravenously on each 2 days over 5 days. ●, untreated; *, one dose of oritavancin 50 mg/kg (Day 1); ★, two doses of oritavancin 50 mg/kg q2d (Days 1 and 3); ◆, three doses of oritavancin 50 mg/kg q2d (Days 1, 3, 5); ◆, three doses of vancomycin 50 mg/kg q2d (Days 1, 3, 5); CL, injection of clinadamycin (100 mg/kg, subcutaneous); CD, infection with *C. difficile* by oral gavage; Tx, injection of antibiotics; ORI, oritavancin; Vanco, vancomycin.

Figure 11A:
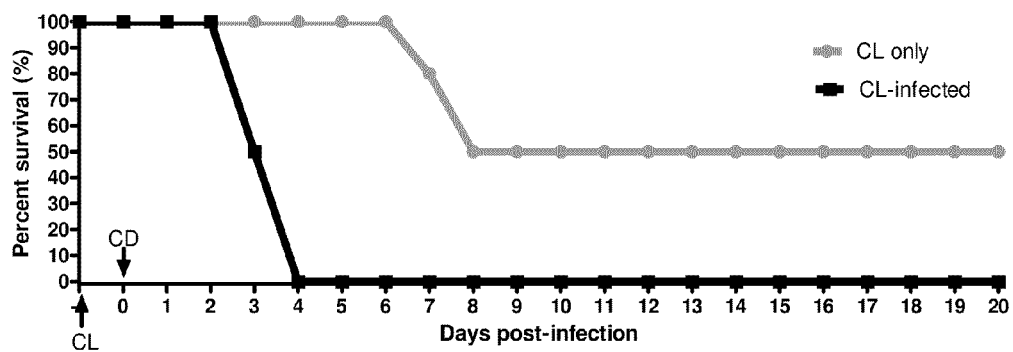

FIG. 11A shows the validation of the hamster model of CDI.

Figure 11B:
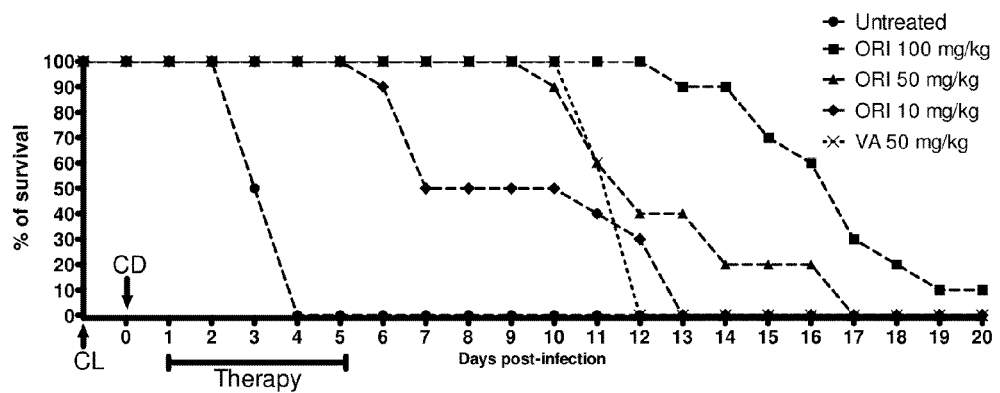

FIG. 11B shows the efficacy of ORI formulated in HPCD compared to VA in the hamster model of CDI.

Figure 11C:
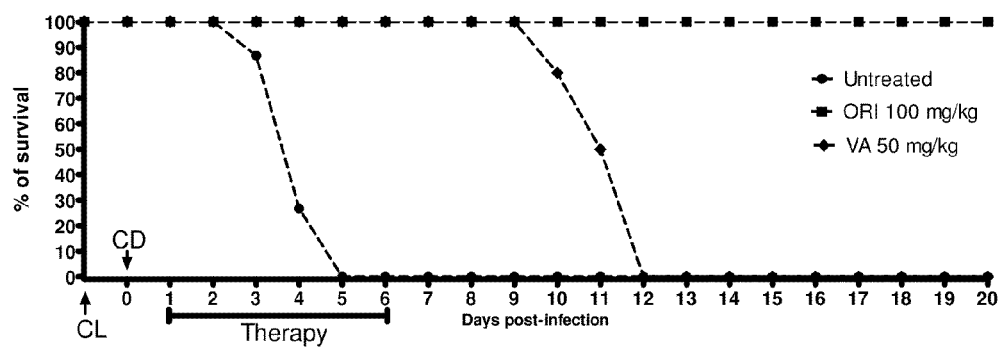

FIG. 11C shows the efficacy of ORI formulated in PEG400 compared to VA in the hamster model of CDI.

Figure 11D:
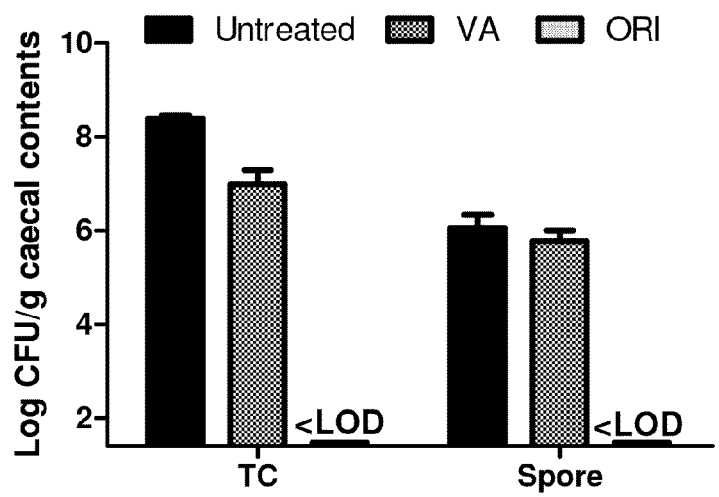

FIG. 11D shows CD total viable counts (TC) and spore counts in hamster caecal contents.

DETAILED DESCRIPTION OF THE INVENTION

Inhibiting Growth of *C. difficile*

The invention is generally directed to methods of inhibiting the growth of the bacteria *C. difficile*, in vitro, in vivo and/or ex vivo, comprising contacting *C. difficile* with a glycopeptide antibiotic in an amount sufficient to inhibit the growth of the bacteria *C. difficile*. *C. difficile* may be in the form of a vegetative cell, a spore or a mixture of both. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is also directed to a method of inhibiting activation of a *C. difficile* spore, either in vitro, in vivo or both, comprising contacting a *C. difficile* spore with a glycopeptide antibiotic in an amount sufficient to inhibit activation of a *C. difficile* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is further directed to a method of inhibiting germination of a *C. difficile* spore, either in vitro, in vivo or both, comprising contacting a *C. difficile* spore with a glycopeptide antibiotic in an amount sufficient to inhibit germination of a *C. difficile* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is additionally directed to a method of inhibiting outgrowth of a *C. difficile* spore, either in vitro, in vivo or both, comprising contacting a *C. difficile* spore with a glycopeptide antibiotic in an amount sufficient to inhibit outgrowth of a *C. difficile* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

Moreover, the invention is directed to a method of inhibiting growth of a vegetative form of *C. difficile*, either in vitro, in vivo or both, comprising contacting a vegetative form of *C. difficile* with a glycopeptide antibiotic in an amount sufficient to inhibit growth of a vegetative form of *C. difficile*. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is directed to a method of inhibiting *C. difficile* sporulation, either in vitro, in vivo or both, comprising contacting a vegetative form of *C. difficile* with a glycopeptide antibiotic in an amount sufficient to inhibit *C. difficile* sporulation. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

Treatment of *C. difficile* Infections

The invention is generally directed to methods of treating a *C. difficile* infection in a subject, comprising administering a therapeutically effective amount of a glycopeptide antibiotic to a subject having a *C. difficile* infection. Preferably, *C. difficile* is in the form of a vegetative cell, a spore or a mixture of both. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

The invention is also directed to a method of treating a *C. difficile* infection in a subject, comprising administering a therapeutically effective amount of a glycopeptide antibiotic to a subject having a *C. difficile* infection, wherein said treatment inhibits activation of a *C. difficile* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

The invention is further directed to a method of treating a *C. difficile* infection in a subject, comprising administering a therapeutically effective amount of a glycopeptide antibiotic to a subject having a *C. difficile* infection, wherein said treatment inhibits germination of a *C. difficile* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

The invention is additionally directed to a method of treating a *C. difficile* infection in a subject, comprising administering a therapeutically effective amount of a glycopeptide antibiotic to a subject having a *C. difficile* infection, wherein said treatment inhibits outgrowth of a *C. difficile* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

Moreover, the invention is directed to a method of treating a *C. difficile* infection in a subject, comprising administering a therapeutically effective amount of a glycopeptide antibiotic to a subject having a *C. difficile* infection, wherein said treatment inhibits growth of a vegetative form of *C. difficile*. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

Moreover, the invention is directed to a method of treating a *C. difficile* infection in a subject, comprising administering a therapeutically effective amount of a glycopeptide antibiotic to a subject having a *C. difficile* infection, wherein said treatment inhibits *C. difficile* sporulation. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

Prevention of *C. difficile* Infections

The invention is generally directed to methods of preventing a *C. difficile* infection in a subject, comprising administering to a subject at risk of *C. difficile* infection an amount of a glycopeptide antibiotic sufficient to prevent *C. difficile* infection. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

Prophylaxis of *C. difficile* Infections

The invention is generally directed to methods for providing prophylaxis of a *C. difficile* infection in a subject, comprising administering to a subject having a *C. difficile* infection an amount of a glycopeptide antibiotic sufficient to achieve prophylaxis of a *C. difficile* infection. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the administering is via intravenous administration or oral administration.

The present invention includes a glycopeptide antibiotic, preferably oritavancin or pharmaceutically acceptable salt, hydrate, or solvate thereof, for use as a medical treatment in the treatment, prophylaxis and/or prevention of *C. difficile* infection in a subject.

The present invention also includes the use of a glycopeptide antibiotic in the manufacture of a medicament for treatment, prophylaxis and/or prevention of *C. difficile* infection in a subject. Preferably, said glycopeptide antibiotic is oritavancin, or pharmaceutically acceptable salt, hydrate, or solvate thereof, or a mixture thereof.

The present invention includes a kit comprising the pharmaceutical composition or a glycopeptide antibiotic of the present invention and written instructions for its use in treatment, prophylaxis and/or prevention of *C. difficile* infection, in a suitable container.

The glycopeptide antibiotics of the present invention include those of Formula I:

Formula I

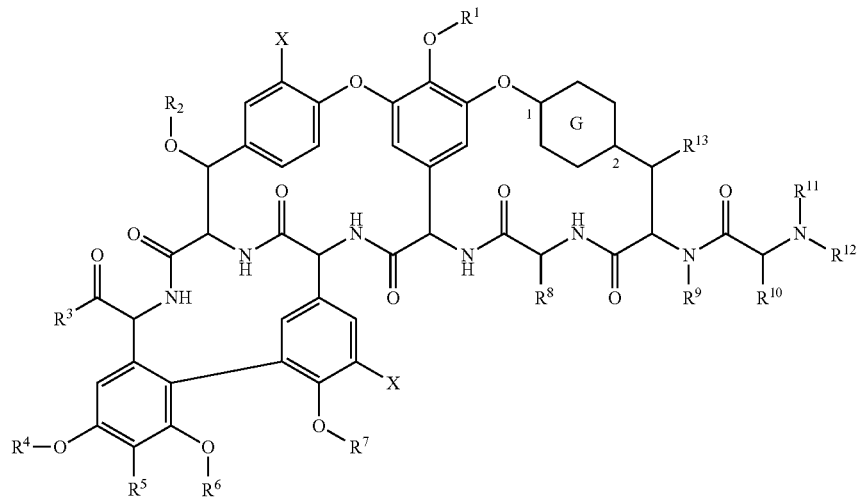

as well as pharmaceutically acceptable salts, hydrates and solvates thereof, and mixtures thereof, wherein:

$R^1$ is one of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$; or $R^1$ is a saccharide group optionally substituted with —$R^a$—$R^b$—$(Z)_x$, —$R^a$—Y—$R^b$—$(Z)_x$, $R^f$, —C(O)$R^f$, or —C(O)—$R^a$—Y—$R^b$—$(Z)_x$;

$R^2$ is hydrogen or a saccharide group optionally substituted with —$R^a$—$R^b$—$(Z)_x$, —$R^a$—Y—$R^b$—$(Z)_x$, $R^f$, —C(O)$R^f$, or —C(O)—$R^a$—Y—$R^b$—$(Z)_x$;

$R^3$ is —$OR^c$, —$NR^cR^c$, —O—$R^a$—Y—$R^b$—$(Z)_x$, —$NR^c$—$R^a$—Y—$R^b$—$(Z)_x$, —$NR^cR^e$, or —O—$R^e$;

$R^4$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, $R^f$, or —C(O)—$R^a$—Y—$R^b$—$(Z)_x$, or $R^4$ and $R^5$ can be joined, together with the atoms to which they are attached, to form a heterocyclic ring optionally substituted with —$NR^c$—$R^a$—Y—$R^b$—$(Z)_x$;

$R^5$ is selected from the group consisting of hydrogen, halo, —CH($R^c$)—$NR^cR^c$, —CH($R^c$)—$NR^cR^e$, —CH($R^c$)—$NR^c$—$R^a$—Y—$R^b$—$(Z)_x$, —CH($R^c$)—$R^x$, and —CH($R^c$)—$NR^c$—$R^a$—C(O)—$R^x$;

$R^6$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, $R^f$, —C(O)$R^f$, or —C(O)—$R^a$—Y—$R^b$—$(Z)_x$, or $R^5$ and $R^6$ can be joined, together with the atoms to which they are attached, to form a heterocyclic ring optionally substituted with —$NR^c$—$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, —$R^a$—Y—$R^b$—$(Z)_x$, and —C(O)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —$Ar^1$—O—$Ar^2$—, where $Ar^1$ and $Ar^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)$R^d$, —C(NH)$R^d$, —C(O)$NR^cR^c$, —C(O)$OR^d$, —C(NH)$NR^cR^c$, —$R^a$—Y—$R^b$—$(Z)_x$, and —C(O)—$R^b$—Y—$R^b$—$(Z)_x$, or $R^{11}$ and $R^{12}$ are joined, together with the nitrogen atom to which they are attached, to form a heterocyclic ring;

$R^{13}$ is selected from the group consisting of hydrogen or —$OR^{14}$;

$R^{14}$ is selected from hydrogen, —C(O)$R^d$ and a saccharide group;

$R^a$ is each independently selected from the group consisting of alkylene, substituted alkylene, alkenylene, substituted alkenylene, alkynylene and substituted alkynylene;

$R^b$ is each independently selected from the group consisting of a covalent bond, arylene, alkylene, substituted alkylene, alkenylene, substituted alkenylene, alkynylene and substituted alkynylene;

$R^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

$R^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^e$ is each a saccharide group;

$R^f$ is each independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic;

$R^x$ is an N-linked amino saccharide or an N-linked heterocycle;

X is each independently selected from hydrogen, fluoro, chloro, bromo or iodo;

Y is each independently selected from the group consisting of, —CH$_2$—, oxygen, sulfur, —S—S—, —NR$^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$, —OC(O)O—, —NR$^c$C(O)O—, —NR$^c$C(O)NR$^c$—, —OC(O)NR$^c$—, —C(O)—, and —N(R$^c$)SO$_2$NR$^c$—;

Z is each independently selected from hydrogen, aryl, cycloalkyl, cycloalkenyl, heteroaryl, heterocyclic; or a saccharide.

x is 1 or 2; and is selected from

In particular, the glycopeptide antibiotics of Formula I include teicoplanin, dalbavancin and telavancin.

The glycopeptide antibiotics of the present invention also include those of Formula II:

Formula II as well as pharmaceutically acceptable salts, hydrates and solvates thereof, and mixtures thereof, wherein:

X and Y are each independently hydrogen or chloro;

R is hydrogen, 4-epi-vancosaminyl, actinosaminyl, ristosaminyl, or a group of the formula —$R^a$—$R^{7a}$, wherein $R^a$ is 4-epi-vancosaminyl, actinosaminyl, or ristosaminyl, and $R^{7a}$, defined below, is attached to the amino group of $R^a$;

$R^1$ is hydrogen or mannose;

$R^2$ is —NH$_2$, —NHCH$_3$, —N(CH$_3$)$_2$, —NHR$^{7b}$, or —N(CH$_3$)R$^{7b}$, wherein $R^{7b}$ is defined below;

$R^3$ is —CH$_2$CH(CH$_3$)$_2$, [p-OH, m-Cl]phenyl, p-rhamnosyloxyphenyl, p-(rhamnosyl-galactosyloxy)-phenyl, [p-galactose-galactose]phenyl, p-(methoxyrhamnosyloxy)phenyl or p-methoxy-rhamnosyloxyphenyl;

$R^4$ is —CH$_2$(CO)NH$_2$, benzyl, [p-OH]phenyl, or [p-OH, m-Cl]phenyl;

$R^5$ is hydrogen, or mannose;

$R^6$ is 4-epi-vancosaminyl, L-acosaminyl, L-ristosaminyl, or L-actinosaminyl;

$R^7$, as defined below, is attached to the amino group of $R^6$; and $R^7$, $R^{7a}$, and $R^{7b}$ are each independently selected from the group consisting of hydrogen, (C$_2$-C$_{16}$)alkenyl, (C$_2$-C$_{12}$)alkynyl, (C$_1$-C$_{12}$ alkyl)-$R^8$, (C$_1$-C$_{12}$ alkyl)-halo, (C$_2$-C$_6$ alkenyl)-$R^8$, (C$_2$-C$_6$ alkynyl)-$R^8$, and (C$_1$-C$_{12}$ alkyl)-O—$R^8$, provided that $R^7$, $R^{7a}$, and $R^{7b}$ are not all hydrogen, and $R^8$ is selected from the group consisting of:

a) multicyclic aryl unsubstituted or substituted with one or more substituents independently selected from the group consisting of:
(i) hydroxy,
(ii) halo,
(iii) nitro,
(iv) (C$_1$-C$_6$)alkyl,
(v) (C$_2$-C$_6$)alkenyl,
(vi) (C$_2$-C$_6$)alkynyl,
(vii) (C$_1$-C$_6$)alkoxy,
(viii) halo-(C$_1$-C$_6$)alkyl,
(ix) halo-(C$_1$-C$_6$)alkoxy,
(x) carbo-(C$_1$-C$_6$)alkoxy,
(xi) carbobenzyloxy,
(xii) carbobenzyloxy substituted with (C$_1$-C$_6$)alkyl, (C$_1$-C$_6$)alkoxy, halo, or nitro,
(xiii) a group of the formula —S(O)$_{n'}$—$R^9$, wherein n' is 0-2 and $R^9$ is (C$_1$-C$_6$)alkyl, phenyl, or phenyl substituted with (C$_1$-C$_6$)alkyl, (C$_1$-C$_6$)alkoxy, halo, or nitro, and (xiv) a group of the formula —C(O)N($R^{10}$)$_2$ wherein each $R^{10}$ substituent is independently hydrogen, ($C_1$-$C_6$)-alkyl, ($C_1$-$C_6$)-alkoxy, phenyl, or phenyl substituted with ($C_1$-$C_6$)-alkyl, ($C_1$-$C_6$)-alkoxy, halo, or nitro;

b) heteroaryl unsubstituted or substituted with one or more substituents independently selected from the group consisting of:
(i) halo,
(ii) ($C_1$-$C_6$)alkyl,
(iii) ($C_1$-$C_6$)alkoxy,
(iv) halo-($C_1$-$C_6$)alkyl,
(v) halo-($C_1$-$C_6$)alkoxy,
(vi) phenyl,
(vii) thiophenyl,
(viii) phenyl substituted with halo, ($C_1$-$C_6$)alkyl, ($C_2$-$C_6$) alkenyl, ($C_2$-$C_6$)alkynyl, ($C_1$-$C_6$)alkoxy, or nitro,
(ix) carbo-($C_1$-$C_6$)alkoxy,
(x) carbobenzyloxy,
(xi) carbobenzyloxy substituted with ($C_1$-$C_6$)alkyl, ($C_1$-$C_6$)alkoxy, halo, or nitro,
(xii) a group of the formula —S(O)$_n$—$R^9$, as defined above,
(xiii) a group of the formula —C(O)N($R^{10}$)$_2$ as defined above, and
(xiv) thienyl;
c) a group of the formula:

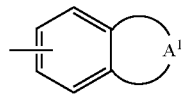

wherein $A^1$ is —OC($A^2$)$_2$-C($A^2$)$_2$-O—, —O—C($A^2$)$_2$-O—, —C($A^2$)$_2$-O—, or —C($A^2$)$_2$-C($A^2$)$_2$-C($A^2$)$_2$-C($A^2$)$_2$-, and each $A^2$ substituent is independently selected from hydrogen, ($C_1$-$C_6$)-alkyl, ($C_1$-$C_6$)alkoxy, and ($C_4$-$C_{10}$)cycloalkyl;

d) a group of the formula:

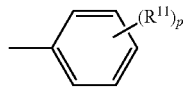

wherein p is from 1 to 5; and $R^{11}$ is independently selected from the group consisting of:
(i) hydrogen,
(ii) nitro,
(iii) hydroxy,
(iv) halo,
(v) ($C_1$-$C_8$)alkyl,
(vi) ($C_1$-$C_8$)alkoxy,
(vii) ($C_9$-$C_{12}$)alkyl,
(viii) ($C_2$-$C_9$)alkynyl,
(ix) ($C_9$-$C_{12}$)alkoxy,
(x) ($C_1$-$C_3$)alkoxy substituted with ($C_1$-$C_3$)alkoxy, hydroxy, halo($C_1$-$C_3$)alkoxy, or ($C_1$-$C_4$)alkylthio,
(xi) ($C_2$-$C_5$)alkenyloxy,
(xii) ($C_2$-$C_{13}$)alkynyloxy
(xiii) halo-($C_1$-$C_6$)alkyl,
(xiv) halo-($C_1$-$C_6$)alkoxy,
(xv) ($C_2$-$C_6$)alkylthio,
(xvi) ($C_2$-$C_{10}$)alkanoyloxy,
(xvii) carboxy-($C_2$-$C_4$)alkenyl,
(xviii) ($C_1$-$C_3$)alkylsulfonyloxy,
(xix) carboxy-($C_1$-$C_3$)alkyl,
(xx) N-[di($C_1$-$C_3$)-alkyl]amino-($C_1$-$C_3$)alkoxy,
(xxi) cyano-($C_1$-$C_6$)alkoxy, and
(xxii) diphenyl-($C_1$-$C_6$)alkyl,
with the proviso that when $R^{11}$ is ($C_1$-$C_8$)alkyl, ($C_1$-$C_8$) alkoxy, or halo, p must be greater or equal to 2, or when $R^7$ is ($C_1$-$C_3$ alkyl)-$R^8$ then $R^{11}$ is not hydrogen, ($C_1$-$C_8$)alkyl, ($C_1$-$C_8$)alkoxy, or halo;

e) a group of the formula:

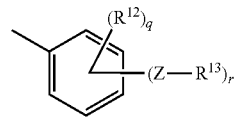

wherein q is 0 to 4; $R^{12}$ is independently selected from the group consisting of:
(i) halo,
(ii) nitro,
(iii) ($C_1$-$C_6$)alkyl,
(iv) ($C_1$-$C_6$)alkoxy,
(v) halo-($C_1$-$C_6$)alkyl,
(vi) halo-($C_1$-$C_6$)alkoxy,
(vii) hydroxy, and
(vii) ($C_1$-$C_6$)thioalkyl,
r is 1 to 5; provided that the sum of q and r is no greater than 5;
Z is selected from the group consisting of:
(i) a single bond,
(ii) divalent ($C_1$-$C_6$)alkyl unsubstituted or substituted with hydroxy, ($C_1$-$C_6$)alkyl, or ($C_1$-$C_6$)alkoxy,
(iii) divalent ($C_2$-$C_6$)alkenyl,
(iv) divalent ($C_2$-$C_6$)alkynyl, and
(v) a group of the formula —(C($R^{14}$)$_2$)$_s$—$R^{15}$— or —$R^{15}$—(C($R^{14}$)$_2$)$_s$—, wherein s is 0-6; wherein each $R^{14}$ substituent is independently selected from hydrogen, ($C_1$-$C_6$)-alkyl, or ($C_4$-$C_{10}$)cycloalkyl; and $R^{15}$ is selected from —O—, —S—, —SO—, —SO$_2$—, —SO$_2$—O—, —C(O)—, —OC(O)—, —C(O)O—, —NH—, —N($C_1$-$C_6$ alkyl)-, and —C(O)NH—, —NHC(O)—, N=N;
$R^{13}$ is independently selected from the group consisting of:
(i) ($C_4$-$C_{10}$)heterocyclyl,
(ii) heteroaryl,
(iii) ($C_4$-$C_{10}$)cycloalkyl unsubstituted or substituted with ($C_1$-$C_6$)alkyl, and
(iv) phenyl unsubstituted or substituted with 1 to 5 substituents independently selected from: halo, hydroxy, nitro, ($C_1$-$C_{10}$)alkyl, ($C_1$-$C_{10}$)alkoxy, halo-($C_1$-$C_3$) alkoxy, halo-($C_1$-$C_3$)alkyl, ($C_1$-$C_3$)alkoxyphenyl, phenyl, phenyl-($C_1$-$C_3$)alkyl, ($C_1$-$C_6$)alkoxyphenyl, phenyl-($C_2$-$C_3$)alkynyl, and ($C_1$-$C_6$)alkylphenyl;

f) ($C_4$-$C_{10}$)cycloalkyl unsubstituted or substituted with one or more substituents independently selected from the group consisting of:
(i) ($C_1$-$C_6$)alkyl,
(ii) ($C_1$-$C_6$)alkoxy,
(iii) ($C_2$-$C_6$)alkenyl,
(iv) ($C_2$-$C_6$)alkynyl,
(v) ($C_4$-$C_{10}$)cycloalkyl,
(vi) phenyl,
(vii) phenylthio,
(viii) phenyl substituted by nitro, halo, ($C_1$-$C_6$)alkanoyloxy, or carbocycloalkoxy, and
(ix) a group represented by the formula —Z—$R^{13}$ wherein Z and $R^{13}$ are as defined above; and g) a group of the formula:

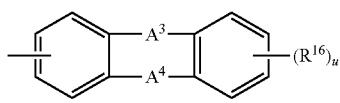

wherein $A^3$ and $A^4$ are each independently selected from
(i) a bond,
(ii) —O—,
(iii) —S(O)$_t$—, wherein t is 0 to 2,
(iv) —C($R^{17}$)$_2$—, wherein each $R^{17}$ substituent is independently selected from hydrogen, $(C_1$-$C_6)$alkyl, hydroxy, $(C_1$-$C_6)$alkyl, $(C_1$-$C_6)$alkoxy, or both $R^{17}$ substituents taken together are O,
(v) —N($R^{18}$)$_2$—, wherein each $R^{18}$ substituent is independently selected from hydrogen; $(C_1$-$C_6)$alkyl; $(C_2$-$C_6)$alkenyl; $(C_2$-$C_6)$alkynyl; $(C_4$-$C_{10})$cycloalkyl; phenyl; phenyl substituted by nitro, halo, $(C_1$-$C_6)$alkanoyloxy; or both $R^{18}$ substituents taken together are $(C_4$-$C_{10})$cycloalkyl;
$R^{16}$ is $R^{12}$ or $R^{13}$ as defined above; and u is 0-4.

The glycopeptide antibiotics of the present invention include each of those disclosed in U.S. Pat. No. 5,840,684, incorporated herein by reference in its entirety.

Oritavancin (also termed N-(4-(4-chlorophenyl)benzyl) A82846B and LY333328) has the following Formula III:

The term "multicyclic aryl" means a stable, saturated or unsaturated, substituted or unsubstituted, 9 to 10 membered organic fused bicyclic ring; a stable, saturated or unsaturated, substituted or unsubstituted 12 to 14 membered organic fused tricyclic ring; or a stable, saturated or unsaturated, substituted or unsubstituted 14 to 16 membered organic fused tetracyclic ring. The bicyclic ring may have 0 to 4 substituents, the tricyclic ring may have 0 to 6 substituents, and the tetracyclic ring may have 0 to 8 substituents. Typical multi-cyclic aryls include fluorenyl, napthyl, anthranyl, phenanthranyl, biphenylene and pyrenyl.

The term "heteroaryl" represents a stable, saturated or unsaturated, substituted or unsubstituted, 4 to 7 membered organic monocyclic ring having a hetero atom selected from S, O, and N; a stable, saturated or unsaturated, substituted or unsubstituted, 9 to 10 membered organic fused bicyclic ring having 1 to 2 hetero atoms selected from S, O, and N; or a stable, saturated or unsaturated, substituted or unsubstituted, 12 to 14 membered organic fused tricyclic ring having a hetero atom selected from S, O, and N. The nitrogen and sulfur atoms of these rings are optionally oxidized, and the nitrogen hetero atoms are optionally quartemized. The monocyclic ring may have 0 to 5 substituents. The bicyclic ring may have 0 to 7 substituents, and the tricyclic ring may have 0 to 9 substituents. Typical heteroaryls include quinolyl, piperidyl, Formula III

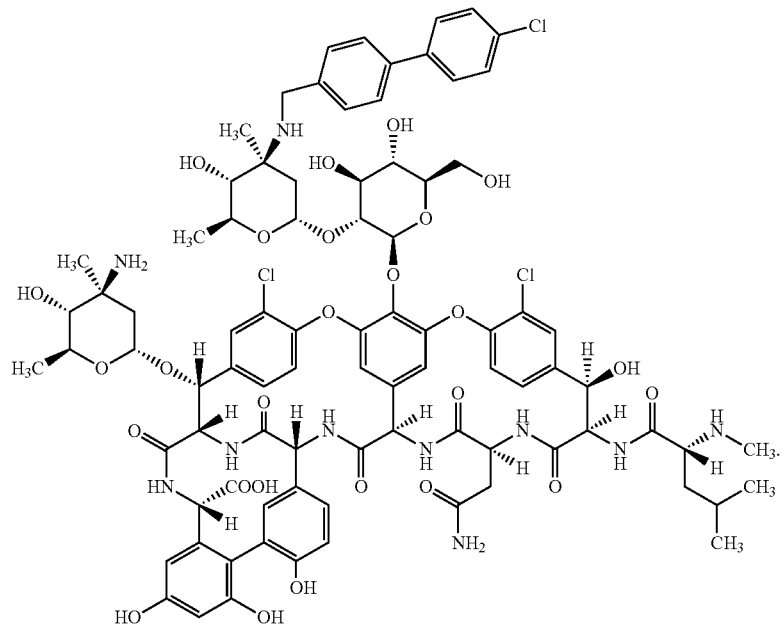

The alkyl substituents recited herein denote substituted or unsubstituted, straight or branched chain hydrocarbons of the length specified. The term "alkenyl" refers to a substituted or unsubstituted, straight or branched alkenyl chain of the length specified herein. The term "alkynyl" refers to a substituted or unsubstituted, straight or branched alkynyl chain of the length specified herein.

The alkoxy substituents recited herein represent an alkyl group attached through an oxygen bridge. The term "alkenoxy" represents an alkenyl chain of the specified length attached to an oxygen atom.

thienyl, piperonyl, oxafluorenyl, pyridyl and benzothienyl and the like.

The term "$(C_4$-$C_{10})$cycloalkyl" embraces substituents having from four to ten carbon atoms, such as cyclobutyl, cyclopentyl, cyclohexyl, and cycloheptyl which may be unsubstituted or substituted with substituents such as alkyl and phenyl. This term also embraces $C_5$ to $C_{10}$ cycloalkenyl groups such as cyclopentenyl and cyclohexenyl. The term "$(C_4$-$C_{10})$cycloalkyl" also embraces bicyclic and tricyclic cycloalkyls such as bicyclopentyl, bicylohexyl, bicycloheptyl, and adamantyl.

The term "alkanoyloxy" represents an alkanoyl group attached through an oxygen bridge. These substituents may be substituted or unsubstituted, straight, or branched chains of the specified length.

The term "cyano-($C_1$-$C_6$) alkoxy" represents a substituted or unsubstituted, straight or branched alkoxy chain having from one to six carbon atoms with a cyano moiety attached to it.

The term "divalent ($C_1$-$C_6$) alkyl" represents an unsubstituted or substituted, straight or branched divalent alkyl chain having from one to six carbon atoms. Typical divalent ($C_1$-$C_6$) alkyl groups include methylene, ethylene, propylene, isopropylene, butylene, isobutylene, secbutylene, t-butylene, pentylene, neo-pentylene, and hexylene. Such divalent ($C_1$-$C_6$) alkyl groups may be substituted with substituents such as alkyl, alkoxy, and hydroxy.

The term "divalent ($C_2$-$C_6$)alkenyl" represents a straight or branched divalent alkenyl chain having from two to six carbon atoms. Typical divalent ($C_2$-$C_6$) alkenyl include ethenyl, 1-propenyl, 2-propenyl, 1-butenyl, 2-butenyl and the like.

The term "divalent ($C_2$-$C_6$) alkynyl" represents a straight or branched divalent alkynyl chain having from two to six carbon atoms. Typical divalent ($C_2$-$C_6$) alkynyl include ethynylene, 1-propynylene, 2-propynylene, 1-butynylene, 2-butynylene and the like.

The term "halo" represents chloro, fluoro, bromo or iodo.

The term "halo-($C_1$-$C_6$)alkyl" represents a straight or branched alkyl chain having from one to six carbon atoms with from 0 to 3 halogen atoms attached to each carbon.

Typical halo-($C_1$-$C_6$) alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like.

The term "halo-($C_1$-$C_6$)alkoxy" represents a straight or branched alkoxy chain having from one to six carbon atoms with from 0 to 3 halogen atoms attached to each carbon.

Typical halo-($C_1$-$C_6$) alkoxy groups include chloromethoxy, 2-bromoethoxy, 1-chloroisopropoxy, 3-fluoropropoxy, 2,3-dibromobutoxy, 3-chloroisobutoxy, iodo-t-butoxy, trifluoromethoxy, and the like.

The term "heterocyclyl" embraces saturated groups having three to ten ring members and which heterocyclic ring contains a hetero atom selected from oxygen, sulfur and nitrogen, examples of which are piperazinyl, morpholino, piperdyl, methylpiperdyl, azetidinyl, and aziridinyl.

The glycopeptide antibiotics of the present invention, including oritavancin, may be used per se or in the form of a pharmaceutically acceptable salt, hydrate, solvate, or mixtures thereof. The term "pharmaceutically acceptable salt" refers to non-toxic acid addition salts derived from inorganic and organic acids.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counter-ion forming a part of any salt of this invention is not of a critical nature, so long as the salt as a whole is pharmacologically acceptable and as long as the counter-ion does not contribute undesired qualities to the salt as a whole.

Means for the preparation of the glycopeptide antibiotics, including oritavancin and analogs thereof, may be found, for example, in U.S. Pat. No. 5,840,684, incorporated herein by reference in its entirety.

The glycopeptide antibiotics of the present invention, including oritavancin, may be also be used in the form of prodrugs, such as glycopeptide antibiotics possessing at least one poly(ethylene glycol) moiety as disclosed in international patent application PCT/US2008/057841, incorporated herein in its entirety. The presence of a poly(ethylene glycol) group attached to a glycopeptide correlates with a higher solubility of the glycopeptide antibiotics in aqueous media. Achieving higher concentrations of glycopeptide antibiotics in aqueous media improves the formulation and reduces the volume of injection, infusion or administration. In addition, the presence of the poly(ethylene) glycol permits the antibiotic to be masked during injection, infusion or administration. The combination of these two factors and the relative lack of toxicity associated with poly(ethylene glycol) allows the side effects observed during the administration of glycopeptide antibiotics to be decreased. In a preferred embodiment, the poly(ethylene glycol) of such prodrugs has an average molecular weight 900 g·$mol^{-1}$ or greater As used herein, a "subject" refers to an animal, such as a mammalian or an avian species, including a human, an ape, a horse, a cow, a sheep, a goat, a dog, and a cat. The subject may have a *C. difficile* infection, may be at risk for developing a *C. difficile* infection, or may be at greater risk than the general population for developing a *C. difficile* infection. Examples of subjects having a higher risk for *C. difficile* infection include patients undergoing treatment for bacterial infections whereby normal gut flora is inhibited by antimicrobial therapy, patients with impaired immune function (e.g., immunoglobulin deficiency, splenic dysfunction, splenectomy, HIV infection, impaired leukocyte function, hemoglobinopathies), the elderly (Loo et al., 2005. NEJM 353:2442), people with certain malignancies (e.g., multiple myeloma, chronic lympocytic leukemia, lymphoma), people at increased occupational risk (e.g., public services workers, such a fire, water, sanitary, police, medical, and laboratory workers, hospital workers), people in closed populations (e.g., prisons, military, nursing homes) and others that have immunological deficiencies that might enhance their susceptibility to bacterial infection.

The methods of the present invention include those performed in vivo, in vitro or ex vivo. The in vitro methods are exemplified, but not limited to, methods performed in a laboratory setting, such as in a cell culture, as well as methods performed on inert objects such as laboratory or hospital equipment and devices, surfaces such as countertops and bench tops. The ex vivo methods are exemplified, but not limited to, methods performed on the surface of the human body, such as on the hands.

The methods of the present invention include both those where one or more glycopeptide antibiotics are used, as well as those where pharmaceutical compositions comprising one or more glycopeptide antibiotics are used. The pharmaceutical compositions of the present invention comprise one or more glycopeptide antibiotics, and one or more of a carrier, diluent and excipient. Suitable carriers, diluents and excipients are well known to those skilled in the art and include saline, buffered saline, dextrose (e.g., 5% dextrose in water), water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717), hydrophilic and hydrophobic carriers, and combinations thereof. Hydrophobic carriers include, for example, fat emulsions, lipids, PEGylated phospholids, polymer matrices, biocompatible polymers, lipospheres, vesicles, particles, and liposomes. The terms specifically exclude cell culture medium.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

Pharmaceutically acceptable excipients also include tonicity agents that make the composition compatible with blood. Tonicity agents are particularly desirable in injectable formulations.

The pharmaceutical compositions and glycopeptide antibiotics of the present invention may be formulated, for example, for oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

Formulations for parenteral administration can be in the form of aqueous or non-aqueous isotonic sterile injection solutions, suspensions or fat emulsions. The parenteral form used for injection must be fluid to the extent that easy syringability exists. These solutions or suspensions can be prepared from sterile concentrated liquids, powders or granules.

Excipients used in parenteral preparations also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of glycopeptide antibiotics can be a ready-to-use solution of the glycopeptide antibiotic in a suitable carrier in sterile, hermetically sealed ampoules or in sterile pre-loaded syringes. The suitable carrier optionally comprises any of the above-mentioned excipients.

Alternatively, the unit dosage of the glycopeptide antibiotics of the present invention can be in a concentrated liquid, powder or granular form for ex tempore reconstitution in the appropriate pharmaceutically acceptable carrier, such as sterile water, at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose in water or Ringer's™ solution.

In intramuscular preparations, a sterile formulation of the pharmaceutical compositions of the present invention can be dissolved and administered in a pharmaceutical diluent such as Water-for-Injection (WFI), physiological saline or 5% dextrose in water. A suitable insoluble form of the pharmaceutical compositions may be prepared and administered as a suspension in an aqueous base or a pharmaceutically acceptable oil base, e.g. an ester of a long chain fatty acid such as ethyl oleate.

For oral use, the oral pharmaceutical composition may be made in the form of a unit dosage containing a therapeutically-effective amount of the pharmaceutical compositions. Solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

For therapeutic purposes, the tablets and capsules can contain, in addition to the glycopeptide antibiotics, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavouring (e.g. peppermint, oil of wintergreen, fruit flavoring, cherry, grape, bubblegum, and the like), and coloring agents. Carriers may also include coating excipients such as glyceryl monostearate or glyceryl distearate, to delay absorption in the gastrointestinal tract.

In a particular oral formulation, the glycopeptide antibiotics of the present invention may be in the form of a capsule containing the glycopeptide antibiotic, gelatin, iron oxide, polyethylene glycol, titanium dioxide, and one or more other inactive ingredients. Suitable amounts of the glycopeptide antibiotic in the capsule may range from about 10 to about 3000 mg, with preferred amounts including about 100, 125, 150, 175, 200, 225, 250, 275, 300, 350, 400, 450, 500, 550, 600, 650, 700, 750, 800, 850, 900, 950, 1000, 1050, 1100, 1150, 1200, 1250, 1300, 1350, 1400, 1450 and 1500 mg of the glycopeptide antibiotic. The oral formulations may also include polyethylene glycol (PEG), wherein the PEG is about PEG200 to about PEG8000, preferably about PEG400 to about PEG6000.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid.

For topical use, the pharmaceutical compositions of present invention can also be prepared in suitable forms to be applied to the skin, or mucus membranes of the nose and throat, and can take the form of creams, ointments, nasal drops, liquid sprays or inhalants, lozenges, or throat paints. Such topical formulations further can include chemical compounds such as dimethylsulfoxide (DMSO) to facilitate surface penetration of the active ingredient. For application to the eyes or ears, the pharmaceutical compositions can be presented in liquid or semi-liquid form formulated in hydrophobic or hydrophilic bases as ointments, creams, lotions, paints or powders. For rectal administration the pharmaceutical compositions can be administered in the form of suppositories admixed with conventional carriers such as cocoa butter, wax or other glyceride.

In a preferred intravenous (IV) formulation for use in the methods of the present invention, oritavancin is administered in a dosage of between about 100 mg and 2000 mg, preferably about 100, 125, 150, 175, 200, 225, 250, 275, 300, 325, 350, 375, 400, 450, 500, 600, 700, 800, 900, 1000, 1100, 1200, 1300, 1400, 1500 or more mg, by IV infusion over approximately 60, 90, 120 or more minutes, every 6, 12, 18 or 24 hours for 1, 2, 3, 4, 5, 6, 7, 8, 9, 10 or more days. In this embodiment, oritavancin may be reconstituted in sterile water for injection (WFI). Further in this embodiment, oritavancin may be diluted in 5% dextrose in water (D5W) to a total volume of at least 250 mL. Preferably the resultant concentration is no more than 0.8 mg/mL for a 200-mg dose, 1.0 mg/mL for a 250-mg dose, and 1.2 mg/mL for a 300-mg dose.

In a preferred oral formulation for use in the methods of the present invention, oritavancin is administered in an oral dosage of between about 0.5 to about 100 mg per kg body weight of the subject to which the oral formulation is being administered, more preferably about 5 to about 30 mg per kg body weight, including about 5, 10, 15, 20, 25 and 30 mg per kg body weight. The course of treatment via oral administration may be a single dose or multiple doses. When multiple doses are administered orally, administration may be once, twice, thrice or more times per day. A course of oral treatment may be for one or more days, such as two, three, four, five, six, seven, eight, nine, ten or more days. In one embodiment, oritavancin may be formulated in 10% hydroxypropyl beta-cyclodextrin. In a further embodiment oritavancin may be formulated in 85% polyethylene glycol 400 (PEG400) in sterile water. The oral formulation may be in the form of a liquid to be drunk by the subject, in the form of a capsule containing the oritavancin formulation, or other means known to the skilled artisan for administering an oral formulation.

Each of the methods of the present invention may also be practiced by including an additional antibacterial agent with the glycopeptide antibiotic or in the pharmaceutical composition. Such antibacterial agents are in addition to the one or more glycopeptide antibiotics that may be used in each of the methods. Additional antibacterial agents include a rifamycin, a sulfonamide, a beta-lactam, a tetracycline, a chloramphenicol, an aminoglycoside, a macrolide, a streptogramin, a quinolone, a fluoroquinolone, an oxazolidinone and a lipopeptide. In particular, tetracycline, tetracycline derived antibacterial agents, glycylcycline, glycylcycline derived antibacterial agents, minocycline, minocycline derived antibacterial agents, oxazolidinone antibacterial agents, aminoglycoside antibacterial agents, quinolone antibacterial agents, vancomycin, vancomycin derived antibacterial agents, teicoplanin, teicoplanin derived antibacterial agents, eremomycin, eremomycin derived antibacterial agents, chloroeremomycin, chloroeremomycin derived antibacterial agents, daptomycin, and daptomycin derived antibacterial agents are preferred.

The terms "dose", "unit dose", "unit dosage", or "effective dose" refer to physically discrete units that contain a predetermined quantity of active ingredient calculated to produce a desired therapeutic effect. These terms are synonymous with the therapeutically effective amounts and amounts sufficient to achieve the stated goals of the methods disclosed herein.

The therapeutically effective amount of the glycopeptide antibiotics of the present invention and the amounts sufficient to achieve the stated goals of the methods disclosed herein vary depending upon the physical characteristics of the subject, the severity of the subject's symptoms, the formulation and the means used to administer the drug, and the method being practiced. The specific dose for a given subject is usually set by the judgment of the attending physician. However, a therapeutically effective and/or sufficient amount of the glycopeptide antibiotics of the present invention, including oritavancin, is typically between about 0.5 mg/kg body weight to 100 mg/kg body weight, preferably from 1 to 50 mg/kg, more preferably from 5 to 30 mg/kg, regardless of the formulation. In equally preferred embodiments, a therapeutically effective amount used for single dosing or infrequent dosing is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 mg/kg body weight, regardless of the formulation. In some situations, a dose less than 0.5 mg/kg body weight or greater than 100 mg/kg body weight may be effective.

Suitable frequencies of administration may vary based on whether administration is for the purposes of treatment, prophylaxis or prevention. Administration frequencies of doses for the treatment of a subject having a *C. difficile* infection, prophylaxis or prevention of *C. difficile* infection include 4, 3, 2 or once daily, every other day, every third day, every fourth day, every fifth day, every sixth day, once weekly, every eight days, every nine days, every ten days, bi-weekly, monthly and bi-monthly. In certain methods and embodiments of the present invention a single dose or infrequent dose (e.g., 2, 3, 4, 5 or six doses) can be sufficient to achieve the stated goals of the methods claimed herein. In other embodiments, the course of treatment may required the administration of many doses over many days, such as administration of a dose 4, 3, 2 or once daily over 1, 2, 3, 4, 5, 6, 7, 8, 9, 10, 11, 12, 13, 14, or more days.

Depending on the means of administration, the dosage may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours.

As used herein, the terms "inhibit", "inhibiting" and "inhibition" have their ordinary and customary meanings, and include one or more of inhibiting growth of a vegetative form of *C. difficile*, inhibiting a function of a vegetative form of *C. difficile*, inhibiting propagation of a vegetative form of *C. difficile*, inhibiting *C. difficile* sporulation, inhibiting activation of a *C. difficile* spore, inhibiting germination of a *C. difficile* spore, and inhibiting outgrowth of a *C. difficile* spore. Such inhibition is an inhibition of about 1% to about 100% of the particular activity versus the activity in a subject to which a pharmaceutical composition or glycopeptide antibiotic of the present invention has not been administered. Preferably, the inhibition is an inhibition of about 100%, 99%, 98%, 97%, 96%, 95%, 90%, 80%, 70%, 60%, 50%, 40%, 30%, 20%, 10%, 5% or 1% of the activity versus a subject to which a pharmaceutical composition or glycopeptide antibiotic of the present invention has not been administered. As used herein, "spore" refers to both the conventionally used terms "spore" and "endospore."

As used herein, the terms "treating" and "treatment" have their ordinary and customary meanings, and include one or more of, ameliorating a symptom of *C. difficile* infection in a subject, blocking or ameliorating a recurrence of a symptom of *C. difficile* infection in a subject, decreasing in severity and/or frequency a symptom of *C. difficile* infection in a subject, stasis, decreasing, or inhibiting growth of a vegetative form of *C. difficile* in a subject, inhibiting *C. difficile* sporulation, inhibiting activation of a *C. difficile* spore in a subject, inhibiting germination of a *C. difficile* spore in a subject, and inhibiting outgrowth of a *C. difficile* spore in a subject. Treatment means ameliorating, blocking, reducing, decreasing or inhibiting by about 1% to about 100% versus a subject to which a pharmaceutical composition or glycopeptide antibiotic of the present invention has not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which a pharmaceutical composition or glycopeptide antibiotic of the present invention has not been administered.

As used herein, the terms "preventing" and "prevention" have their ordinary and customary meanings, and includes one or more of preventing colonization of *C. difficile* in a subject, preventing an increase in the growth of a population of *C. difficile* in a subject, preventing activation, germination or outgrowth of *C. difficile* spores in a subject, preventing sporulation of *C. difficile* in a subject, preventing development of a disease caused by *C. difficile* in a subject, and preventing symptoms of a disease caused by *C. difficile* in a subject. As used herein, the prevention lasts at least about 0.5, 1, 2, 3, 4, 5, 6, 7, 8, 9, 10, 12, 14, 16, 18, 20, 25, 30, 35, 40, 45, 50 or more days after administration of a pharmaceutical composition or glycopeptide antibiotic of the present invention As used herein, "prophylaxis" includes inhibiting the development of a productive or progressive infection by *C. difficile* in a subject, where the prophylaxis lasts at least about 0.5, 1, 2, 3, 4, 5, 6, 7, 8, 9, 10, 12, 14, 16, 18, 20, 25, 30, 35, 40, 45, 50 or more days after administration of a pharmaceutical composition or glycopeptide antibiotic of the present invention. Inhibition against development of a productive or progressive infection by *C. difficile* infection means that the severity of a *C. difficile* infection in a subject is reduced by about 1% to about 100% versus a subject to which a pharmaceutical composition or glycopeptide antibiotic of the present invention has not been administered. Preferably, the reduction in severity is an about 100%, 99%, 98%, 97%, 96%, 95%, 90%, 80%, 70%, 60%, 50%, 40%, 30%, 20%, 10%, 5% or 1% reduction in severity. The severity of an infection may be based on the amount of *C. difficile* present in a subject, the length of time that *C. difficile* can be detected in a subject, and/or the severity of a symptom of *C. difficile* infection, among other factors.

As used herein, the term "bi-weekly" refers to a frequency of every 13-15 days, the term "monthly" refers a frequency of every 28-31 days and "bi-monthly" refers a frequency of every 58-62 days.

As used herein, the term "contacting" is meant to broadly refer to bringing a bacterial cell and a molecule of a glycopeptide antibiotic of the present invention into sufficient proximity that the glycopeptide antibiotic can exert an effect on the bacterial cell. The glycopeptide antibiotic may be transported to the location of the bacterial cell, or the glycopeptide antibiotic may be situated in a location to which the bacterial cell travels or is brought into contact. The skilled artisan will understand that the term "contacting" includes physical interaction between a glycopeptide antibiotic and a bacterial cell, as well as interactions that do not require physical interaction.

As used herein, *C. difficile* refers to all *C. difficile* strain, species and subspecies. PCR ribotyping may be used to distinguish between different *C. difficile* strains, species and subspecies. As an example only, *C. difficile* strain encompassed within the scope of this invention include *C. difficile* PCR ribotypes 001, 106 and 027.

EXAMPLES

Example 1

In these studies, the activity of metronidazole (MET), vancomycin (VAN), and oritavancin (ORI) against *C. difficile* spores was evaluated using three experimental methods: spiral gradient endpoint analysis, agar-based culture and phase-contrast microscopy.

C. difficile Spore Preparation

C. difficile PCR ribotypes 001, 106 and 027 were inoculated onto Columbia blood agar and incubated anaerobically (37° C.) for 10 d. Growth was harvested into sterile saline and alcohol shocked in an equal volume of 100% ethanol for 1 h. Alcohol-shocked spore suspensions were mixed by vortexing and sonicated for 5 minutes at room temperature. C. difficile phase-bright (non-germinated) spores were separated from phase-dark (germinated) spores and cellular debris by density gradient centrifugation (4000 rpm 15 minutes) following layering onto 50% (v/v in phosphate buffered saline) Urografin 370 (Schering, Germany). The density gradient centrifugation step was performed twice. Pellets of purified spores were re-suspended in sterile saline (1 mL per 10 Columbia blood agar plates harvested). Percentage phase-bright spores, phase-dark spores and vegetative cells were recorded using phase-contrast microscopy (×100 magnification).

Spiral Gradient Endpoint Analysis

Figure 1:
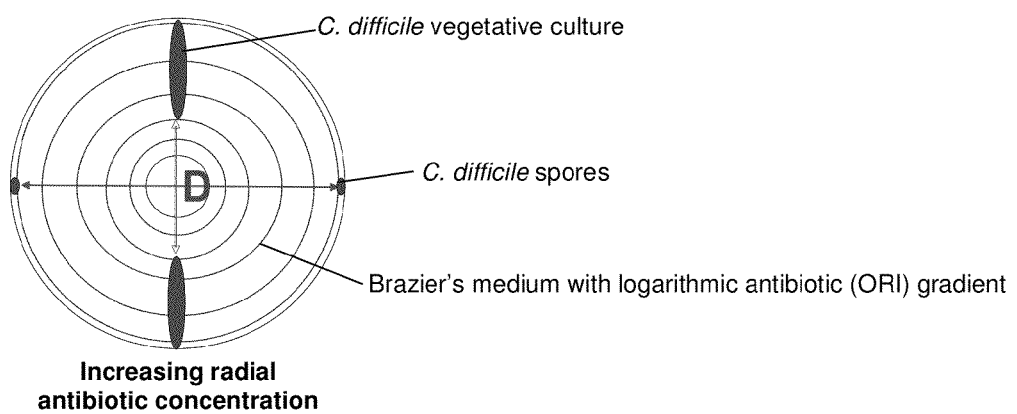
FIG. 1 is a schematic representation of spiral gradient endpoint analysis for MIC determination.

Antimicrobial stock solutions were prepared in de-ionised water (metronidazole, vancomycin)±0.002% polysorbate-80 (oritavancin). A spiral plater (WASP2, Don Whitley Scientific, UK) was used to apply a logarithmic antibiotic gradient onto the surface of pre-dried (37° C. 20 minutes) Brazier's agar (pH 7). Agar with logarithmic antimicrobial gradients applied to their surface remained at room temperature for 1 h to allow the antimicrobial agent to adsorb into the agar. C. difficile vegetative cultures and spores (~$10^7$ cfu/mL) were inoculated onto the agar surface (FIG. 1) with a sterile cotton swab and incubated anaerobically (37° C., 24 h). D-values were measured (in mm) and converted to MICs (Paton, J. H. 1990. *Int J Exp Clin Chemother.* 9, 31-38).

Figure 2:
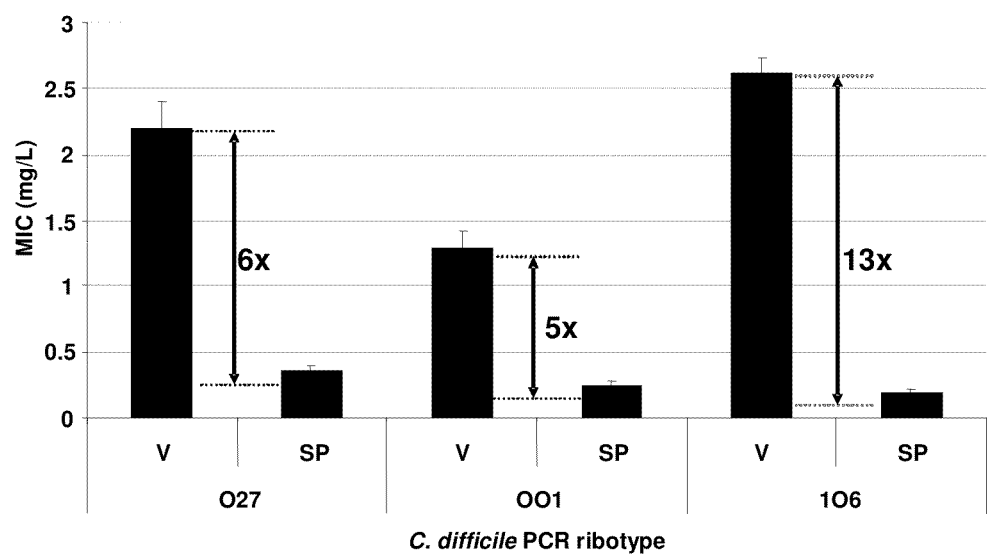
FIG. 2 shows the geometric mean (±SE) oritavancin (ORI) MICs for *C. difficile* vegetative cultures (V) and spores (SP) by spiral gradient endpoint analysis.

ORI MICs against C. difficile spores were 5-13 fold lower than against vegetative cells (FIG. 2). MET and VAN MICs did not differ substantially for C. difficile vegetative cells and spores (data not shown).

Agar-Based Culture

Figure 3:
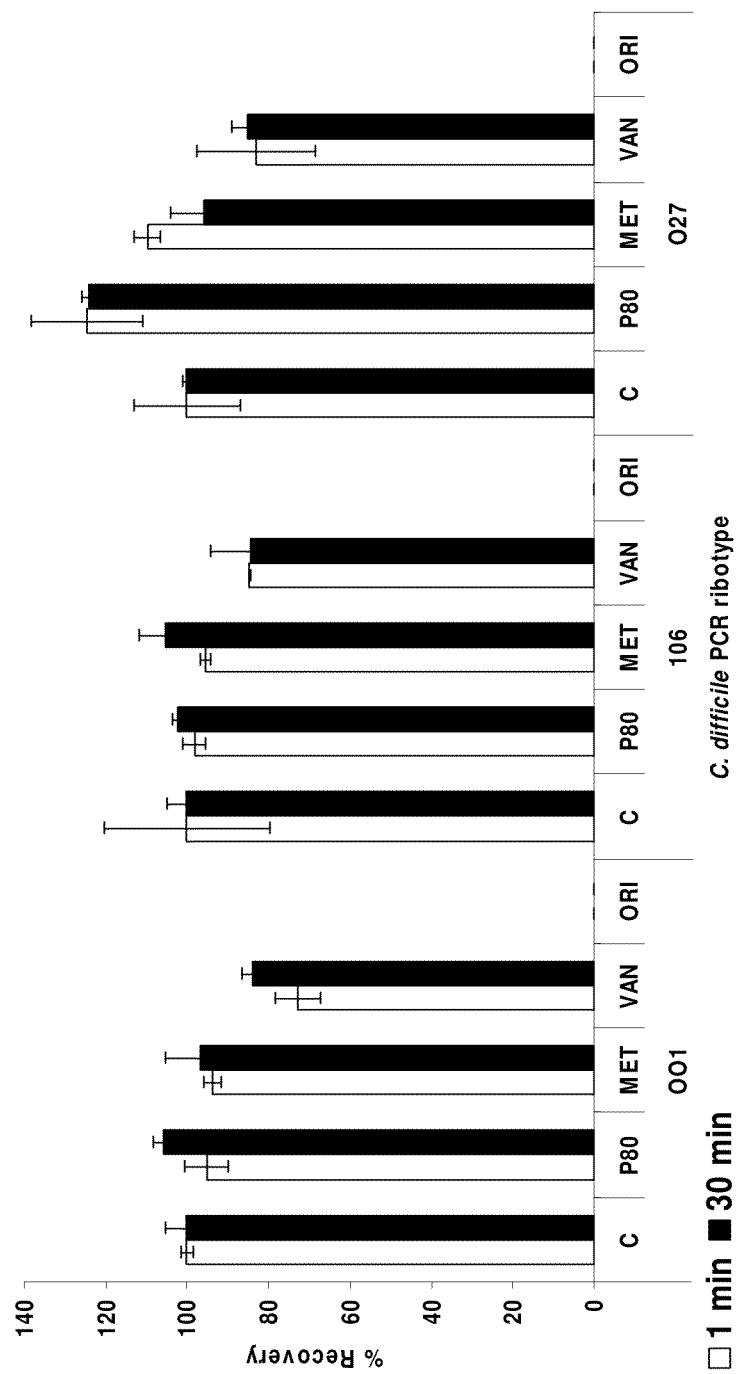
FIG. 3 shows the percent (±range) recovery of *C. difficile* spores exposed for 1 or 30 mins to in vivo concentrations of metronidazole (MET), vancomycin (VAN), ORI, de-ionised water (C) or Tween 80 (P-80).

A standard inoculum of C. difficile spores (~300 cfu) was exposed to (expected in vivo concentrations of) metronidazole (9.3 mg/L), vancomycin (350 mg/L) or oritavancin (350 mg/L) for 1 min and 30 min in triplicate. Antimicrobial-spore solutions were mixed, diluted (to sub-MIC) in sterile de-ionised water, filtered onto cellulose acetate filters (CAF, 0.45 µm) and washed. CAF were transferred onto Brazier's agar (pH 7)+5 mg/L lysozyme, and following anaerobic incubation (37° C., 48 h), % C. difficile spores (vs. control) were determined. C. difficile spores were not recovered following exposure to oritavancin (FIG. 3). Evidence of oritavancin binding to C. difficile spores and CAF was observed (data not shown).

Phase-Contrast Microscopy

Figure 4:
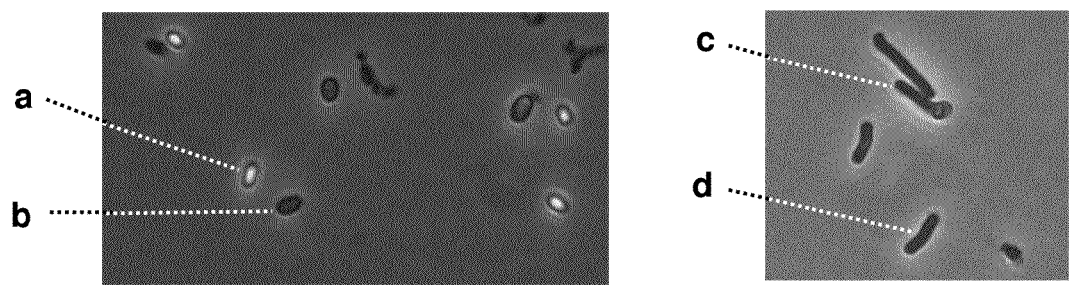
FIG. 4 shows *C. difficile* a) phase bright spores, b) phase dark spores, c) outgrowing spore, d) vegetative cell under phase-contrast microscopy (×100 magnification).

A standard inoculum of C. difficile PCR ribotype 027 spores (~$10^7$ cfu/mL) was suspended in 30 mL Brazier's broth (pH 7) medium incorporating 0.1, 1 or 10 mg/L metronidazole, vancomycin or oritavancin. C. difficile spores were also exposed to 10 mg/L antimicrobial for 2 h, washed 3× in sterile PBS, re-suspended and inoculated into Brazier's broth medium (pH 7). Samples were removed at 2, 4, 6, 24, 32 and 48 h. Slides were viewed under phase-contrast microscopy and percentages of phase-bright spores, phase-dark spores and vegetative cells were recorded (FIG. 4).

Figure 5:
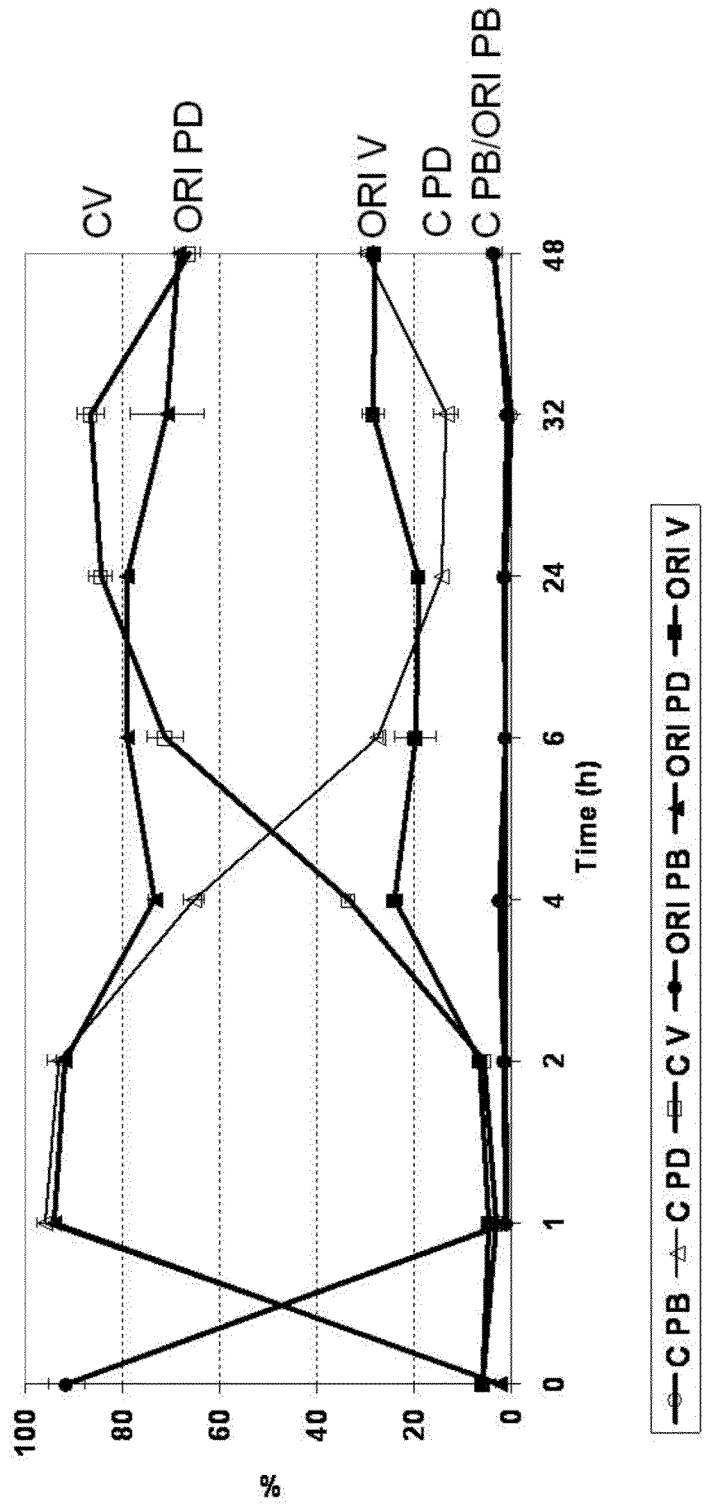
FIG. 5 shows percent (±range) recovery of *C. difficile* PCR ribotype 027 phase-bright (PB) spores, phase-dark (PD)

Statistical analyses were performed by transforming percentage data using an Arcsin Transformation and analysed using a Wilcoxon signed rank test. $P<0.05$ was considered statistically significant. Supra-MIC concentrations of all antimicrobials prevented outgrowth but not germination of C. difficile spores. Outgrowth C. difficile spores prior-exposed to oritavancin was much lower than control ($P=0.058$), and significantly lower than spores prior-exposed MET or VAN ($P<0.05$) (FIG. 5).

Comments

The magnitude of difference in oritavancin MIC against vegetative C. difficile vs. spores was marked and reproducible (MICs were determined on six occasions). Such a phenomenon is not believed to have been previously reported. In vivo, this could afford oritavancin an advantage over existing antimicrobial therapies for CDI, by potentially allowing greater recovery of the gut microflora (which can be expected to be inhibitory to C. difficile) before oritavancin concentrations became sub-inhibitory to C. difficile spore outgrowth.

Spore germination/outgrowth experiments using phase-contrast microscopy demonstrated that all antimicrobials evaluated at supra-MIC levels inhibited C. difficile spore outgrowth but not germination itself. Interestingly, outgrowth of C. difficile PCR ribotype 027 spores prior-exposed to 10 mg/L oritavancin was significantly inhibited despite thorough washing. This phenomenon was not observed for spores prior-exposed to metronidazole or vancomycin at an identical antimicrobial concentration. The peptide antimicrobial nisin was previously demonstrated to be inhibitory to spore outgrowth of *Bacillus subtilis* and *Clostridium sporogenes* (Chan et al. 1996. *Appl Environ Microbiol.* 62, 2966-2969; Rayman et al. 1981. *Appl Environ Microbiol.* 41, 375-380). Oritavancin is functionally related to lipid II binding antimicrobials such as nisin, and recent studies indicate that the drug may also inhibit transglycosylase enzymes involved in polymerising peptidoglycan (Wang et al. 2007. 47th ICAAC Chicago. Poster C1-1474). The mechanism of inhibitory activity against outgrowing C. difficile spores remains to be elucidated, but may potentially be a consequence of oritavancin binding directly to spores.

Example 2

Additional studies regarding the activity of oritavancin (ORI) versus metronidazole (MET) and vancomycin (VAN) on genotypically distinct C. difficile strains were conducted using agar incorporation and broth microdilution methods.

Materials and Methods

Bacterial Strains

Thirty-three genotypically distinct (by PCR ribotyping) C. difficile isolates were selected from a library of strains at the Leeds General Infirmary (Leeds, UK). Representative isolates of epidemic C. difficile PCR ribotypes 001, 106 and 027 were included in the panel. Control isolates of *Staphylococcus aureus* ATCC 29213, *Enterococcus faecalis* ATCC 29212 and *Bacteroides fragilis* ATCC 25285 were included in all MIC determinations to ensure procedure accuracy.

MIC Determination

Agar incorporation MICs were determined based on the method of Freeman and Wilcox (*J Antimicrob Chemother* 2001; 47: 244-6). Briefly, bacteria were cultured in Schaedler's anaerobic broth (Oxoid, Basingstoke, UK) at 37° C. for 24 h in an anaerobic cabinet (Don Whitley Scientific, Shipley). Stock solutions of metronidazole and vancomycin (Sigma-Aldrich Co., Poole, UK) were prepared in de-ionized water. Oritavancin was prepared in 0.002% P80. All antimicrobial solutions were sterilized by filtration through 0.22 um syringe filters. Oritavancin was filtered at 1280 mg/L as filtration at lower concentrations leads to significant proportional losses of drug owing to saturable binding. Wilkins Chalgren agar (Oxoid) incorporating doubling dilutions of antimicrobial agents (0.03-16 mg/L) was prepared with and without 0.002% P80 and with and without 2% lysed horse blood (E&O Labs, Bonneybridge, UK). All media and diluents were pre-reduced overnight in the anaerobic cabinet. Bacterial cultures were diluted in sterile saline and inoculated onto the surface of agar incorporation agar plates using a multipoint inoculator (~$10^4$ cfu). Agar incorporation plates were incubated anaerobically for 48 h. MIC endpoints were read as the lowest concentration of antimicrobial agent where there is no apparent growth (disregarding a visible haze of growth or a single colony).

Broth macrodilution MICs were determined following the method of Jousimies-Somer et al. (Introduction to anaerobic bacteriology. In: Wadsworth-KTL Anaerobic Bacteriology Manual, 6th edn. Belmont, Calif.: Star Publishing Company, 2002; 1-22). Briefly, double-strength antimicrobial stock solutions were prepared in *Brucella* broth (Sigma) supplemented with haemin (5 mg/L, Sigma), NaHCO$_3$ (1 mg/L, Sigma) and vitamin K$_1$ (10 µL/L, Sigma). All broths for oritavancin MICs contained 0.002% P80 (Arhin et al., Abstracts of the Seventeenth European Congress of Clinical Microbiology and Infectious Diseases, Munich, Germany, 2007. Abstract P-827, p. 102. Eur. Soc. Clin. Micro. Infect. Dis., Basel, Switzerland). Bacterial strains were initially cultured overnight in Schaedler's anaerobic broth and subsequently diluted 1:200 (~$3\times10^5$ cfu/mL) in sterile pre-reduced supplemented *Brucella* broth. Antimicrobial stock solutions were diluted 1:2, following the addition of each strain inoculum. Broths were incubated anaerobically at 37° C. for 48 h. MIC endpoints were read as the concentration of antimicrobial agent where no growth was observed compared with the control. MICs were determined in duplicate for all antimicrobial agents.

Results

The activity of oritavancin was evaluated against 33 genotypically distinct *C. difficile* isolates using both agar incorporation and broth macrodilution methods. The panel of *C. difficile* strains used in this study included a representative isolate of PCR ribotype 027, the strain linked to recent epidemics of CDI in Europe, Canada and the USA (Kuijper et al., *Curr Opin Infect Dis* 2007; 20: 376-83). The MICs for genotypically distinct *C. difficile* are shown in Table 1.

TABLE 1

Susceptibilities (mg/L) of genotypically distinct *C. difficile* (n = 33) to oritavancin, metronidazole and vancomycin.

|  |  | MIC$_{90}$ (range) GEO MIC | | |
|---|---|---|---|---|
|  |  | oritavancin | metronidazole | vancomycin |
| BM |  | 1 (0.06-1) 0.31 | 2 (0.125-2) 0.56 | 2 (0.5-2) 1.58 |
| AI | P80 with LHB | 4 (1-4) 1.58 | 2 (0.125-2) 0.55 | 1 (0.5-2) 1.00 |
| AI | P80 no LHB | 4 (2-4) 2.70 | 2 (0.25-2) 0.55 | 2 (1-4) 1.30 |
| AI | no P80 with LHB | 2 (0.5-4) 1.72 | 2 (0.5-4) 0.69 | 2 (1-4) 1.35 |
| AI | no P80 no LHB | 4 (2-4) 2.33 | 2 (0.25-4) 0.53 | 2 (0.5-2) 1.51 |

P80, 0.002% polysorbate-80; LHB, 2% lysed horse blood; BM, broth macrodilution; AI, agar incorporation; Geo MIC, geometric mean MIC.

Metronidazole agar incorporation geometric mean MICs were 2- to 5-fold lower than oritavancin MICs and 2- to 3-fold lower than vancomycin MICs. Oritavancin and vancomycin were similarly active against *C. difficile* for all agar conditions. Supplementation of Wilkins Chalgren agar with 0.002% P80 and 2% lysed horse blood did not greatly influence MICs of oritavancin (or vancomycin and metronidazole) for *C. difficile* or control organisms. Furthermore, incorporation of P80 with or without lysed horse blood did not affect the growth of *C. difficile* or control organisms on non-antimicrobial-containing (control) agar. Broth macrodilution MICs were 2- to 4-fold lower than agar incorporation MICs for oritavancin but not for metronidazole or vancomycin. Oritavancin broth macrodilution geometric mean MICs were ~2- and 5-fold lower than those for metronidazole and vancomycin, respectively. When comparing individual *C. difficile* strain broth macrodilution MICs, 76% (25/33) of tested isolates were more susceptible to oritavancin (≥2 doubling dilutions) than to vancomycin.

Arhin et al. (*Antimicrob Agents Chemother* 2008; 52: 1597-603) recently reported that oritavancin was rapidly lost from the solution in broth microdilution susceptibility assay test plates in the absence of P80 or 2% lysed horse blood. Prior studies have suggested incorporation of P80 or lysed horse blood may significantly reduce oritavancin MICs for staphylococci and enterococci (but not clinical streptococcal isolates) using broth microdilution methods (*Antimicrob Agents Chemother* 2008; 52: 1597-603; Arhin et al., Abstracts of the Seventeenth European Congress of Clinical Microbiology and Infectious Diseases, Munich, Germany, 2007. Abstract P-827, p. 102. Eur. Soc. Clin. Micro. Infect. Dis., Basel, Switzerland). The authors postulated that the presence of lysed blood in culture media used to evaluate clinical streptococcal isolates may have abrogated oritavancin binding to surfaces; hence, the incorporation of P80 did not facilitate any further reduction in oritavancin MICs. Additionally, inclusion of P80 in agar incorporation methods does not reduce oritavancin MICs for *S. aureus*, coagulase negative staphylococci, *E. faecalis* or *Enterococcus faecium*. The present study evaluated the effect of P80 and lysed horse blood on oritavancin, vancomycin and metronidazole MICs using agar incorporation. The presence of P80+lysed horse blood in agar incorporation methods did not substantially reduce oritavancin MICs, thus reflecting previous agar-based MIC studies with facultative anaerobes and highlighting MIC variability between methods. Additionally, incorporation of P80+lysed horse blood in the present study did not affect vancomycin (or metronidazole) MICs, which also reflects prior in vitro susceptibility studies that did not demonstrate a shift in MICs of these antimicrobial agents in the presence of P80 or lysed horse blood (Blosser et al., Abstracts of the 103rd Meeting of the American Society for Microbiology, Washington, D.C., 2003. Abstract C-70. American Society for Microbiology, Washington, D.C., USA).

Assays of oritavancin concentrations in samples collected from an in vitro triple-stage chemostat human gut model using large-plate bioassay indicate that diffusion of the drug in agar is slow; a pre-incubation diffusion step is required to enhance zone diameters. Glycopeptides are known to bind to polymer surfaces (Wilcox et al., *J Antimicrob Chemother* 1994; 33: 431-41), a property that is influenced by surface charge of both the antimicrobial and polymer. For example, binding of teicoplanin to the surfaces of specimen vessels was on average four times greater than that of vancomycin. Pre-exposure of a polymer surface to human body fluids markedly reduces the binding of teicoplanin. Oritavancin is a semi-synthetic lipoglycopeptide that possesses either a single or double positive charge at neutral pH. Therefore, complexing of oritavancin with components of agar, due to physicochemical properties of the antibiotic, may explain the elevated MICs (compared with those measured by broth macrodilution) for *C. difficile* and other bacteria. Indeed, adsorption of antimicrobial peptides to agar surfaces has been reported previously (Boman et al., *FEBS Lett* 1989; 259: 103-6). The present study included all permutations of P80 and lysed horse blood in agar incorporation MICs and showed that neither of the two supplements significantly impacted the assessment of oritavancin susceptibility. Elevated oritavancin agar incorporation MICs compared with both broth micro- and macrodilution MICs have been observed in other institutions, but the definitive mechanism behind this phenomenon remains unexplained (Blosser et al., Abstracts of the 103rd Meeting of the American Society for Microbiology, Washington, D.C., 2003. Abstract C-70. American Society for Microbiology, Washington, D.C., USA)).

Example 3

Comparative Effects of Antibiotic Exposure on Viability of Clostridium difficile Spores Using different experimental methods, oritavancin was demonstrated to disrupt the transition from dormant C. difficile spore to vegetative cell to a greater extent than existing therapeutic antimicrobials for CDI.

Experiments were conducted to determine the independent effects of metronidazole, vancomycin and oritavancin on the viability of C. difficile spores exposed to these antibiotics. The experiments were in general performed by mixing C. difficile spores with an antibiotic, filtering the solution through cellulose acetate filters to collect the spores, applying the spore-containing filters to nutrient agar, and determining the number of spores remaining on the filters after a selected period of time.

Prior experiments have suggested antimicrobial agents may be able to bind cellulose acetate filters despite washing, thus residual antimicrobial may reduce recovery of C. difficile spores. Therefore, the initial experiment included dilution of antimicrobial-containing spore suspensions prior to filtration and washing. Reaction volumes were 1 mL for all antimicrobial/control solutions. Vancomycin and oritavancin were diluted 1:250 and metronidazole was diluted 1:50 in order to effectively reduce antimicrobial concentration to sub-MIC levels prior to filtration.

Example 3A 1 mL of control (de-ionised water+/−Tween-80) and test (antimicrobial containing) solutions were inoculated with 10 µL C. difficile spores (3 strains; PCR ribotypes 001, 106 and 027). Spore suspensions (time=1 min or 30 min) were transferred to filtration cupules and the appropriate volume of diluent (sterile de-ionised water+/−Tween-80) was added to achieve the dilution factors noted above. Samples were filtered onto cellulose acetate filters and washed with a further 50 mL of the appropriate diluent. Filters were transferred aseptically to Braziers CCEY agar containing 5 mg/L lysozyme and 2% lysed horse blood. This procedure was completed in duplicate. The culture media were incubated in an anaerobic atmosphere at 37° C. for 48 h and the numbers of C. difficile colonies were recorded.

The results are shown in FIG. 6. No substantial difference in C. difficile spore recovery was observed between 1 min and 30 min for any given control/treatment. The presence of Tween-80 (P80) did not affect C. difficile spore recovery. Recovery of C. difficile spores at both 1 min and 30 min following exposure to metronidazole ranged from 90-110% of controls. Recovery of C. difficile spores at both 1 min and 30 min following exposure to vancomycin (VAN) ranged from 25-60% of controls. Recovery of C. difficile spores at both 1 min and 30 min following exposure to oritavancin (ORI) was 0%.

These results suggested: 1) glycopeptide antimicrobials may possess anti-C. difficile spore activity, and/or 2) despite dilution of solutions prior to filtration and washing of the filtered spore samples, residual antimicrobial was present in cellulose acetate filters which was inhibitory to germination and/or outgrowth of C. difficile spores Example 3B In order to assess whether the glycopeptide antimicrobials were potentially binding to the cellulose acetate filters prior to or during the addition of diluent, the experimental procedure was modified.

Diluent was first added to filtration cupules. 1 mL reactions were then added to the appropriate diluent (1 min and 30 min after reaction formation) and filtered onto cellulose acetate filters. The filters were washed with 50 mL of the appropriate diluent. The filters were then transferred aseptically to Braziers CCEY agar containing 5 mg/L lysozyme and 2% lysed horse blood. This procedure was completed in duplicate. Culture media were incubated in an anaerobic atmosphere at 37° C. for 48 h and the numbers of C. difficile colonies recorded.

The results are shown in FIG. 7. No substantial difference in C. difficile spore recovery was observed between 1 min and 30 min for any given control/treatment. The presence of Tween-80 (P80) did not affect C. difficile spore recovery. Recovery of C. difficile spores following exposure to metronidazole 95-110% of controls. Recovery of C. difficile spores following exposure to vancomycin increased to 70-80% of controls. Recovery of C. difficile spores at both 1 min and 30 min following exposure to oritavancin (ORI) was 0%.

These results suggested: 1) the design of Experiment 2B aided recovery of C. difficile spores from vancomycin-containing solutions but did not affect recovery from oritavancin-containing solutions, 2) therefore, either oritavancin possesses anti-spore activity or residual antimicrobial remained within filters despite modification of the experimental procedure.

Example 3C

Additional controls were included for vancomycin and oritavancin following Experiment 2B.

One mL solutions (containing no C. difficile spores) were processed as in Experiment 2B and filters placed onto Braziers CCEY agar. Onto the filters were inoculated 2×20 µL of:

a) Vegetative C. difficile (an overnight culture of PCR ribotype 001)

b) C. difficile spores (PCR ribotype 001), or c) Staphylococcus aureus NCTC 6571 (Oxford strain, overnight culture).

Growth/no growth was recorded following anaerobic incubation.

The results showed that all organisms grew on filters through which vancomycin had been filtered. S. aureus NCTC 6571 grew on filters through which oritavancin had been filtered (MIC against this strain is ~4 mg/L via agar incorporation methodology). Greatly reduced numbers of vegetative C. difficile were recovered (1 cfu on one plate) on oritavancin-exposed filters compared to growth on vancomycin-exposed filters. C. difficile spores were unrecoverable from oritavancin-exposed filters despite good growth on vancomycin-exposed filters.

Therefore, these results suggested inhibitory levels of oritavancin persisted in cellulose acetate filters despite the precautions outlined above. The presence of a very small amount of growth from vegetative *C. difficile* cultures in comparison to no spore recovery may suggest a difference in the concentration of oritavancin able to inhibit these forms of *C. difficile*.

Example 3D

A further potential explanation for the failure to recover oritavancin-treated *C. difficile* spores from the above experiments (in addition to presence of the drug in cellulose acetate filters) is that oritavancin may be able to bind *C. difficile* spores and directly damage spores, or inhibit spore germination and/or outgrowth. A simple experiment was conducted in order to assess antimicrobial-spore binding:

Two solutions were prepared:
1) *C. difficile* spores (PCR ribotype 001, control), and
2) *C. difficile* spores suspended in 350 mg/L oritavancin (diluent: Tween-80-$H_2O$).

Fresh blood agar was inoculated with a lawn of the Oxford *S. aureus*. In one replicate, *C. difficile* spores were centrifuged (16000 g, 5 min), the supernatants removed and pellets resuspended in 500 μL of Tween-80-$H_2O$. 10 μL of the resuspended spore suspension was inoculated onto the surface *S. aureus* lawn.

In another replicate, *C. difficile* spore suspensions were washed a total of 10 times using this procedure and inoculated onto the surface of the *S. aureus* lawn.

In both replicates agar was incubated aerobically at 37° C. overnight, and then the presence or absence of zones of inhibition were recorded.

Tween-80 was not inhibitory to growth of the Oxford *S. aureus*. *C. difficile* spores (control) were not inhibitory to growth of the Oxford *S. aureus*. Oritavancin-exposed *C. difficile* spores were inhibitory to growth of the Oxford *S. aureus* after 0, 1, 2, 4, 5, 6, 9, and 10 washes. Therefore, washing of spore suspensions did not remove the antimicrobial effect. These results suggested that oritavancin may directly bind *C. difficile* spores.

Example 4

Comparison of Oritavancin Versus Vancomycin as Treatments for Clindamycin-Induced *C. difficile* PCR Ribotype 027 Infection in a Human Gut Model An in vitro human gut model was used to compare the efficacy of oritavancin and vancomycin for the treatment of clindamycin-induced CDI caused by epidemic *C. difficile* PCR ribotype 027.

Materials and Methods
*C. difficile* Strains

A single isolate of *C. difficile* PCR ribotype 027 was investigated. This isolate was a clinical strain recovered during an epidemic of CDI at the Maine Medical Centre (Portland, USA) in 2005. It was supplied courtesy of Dr. Rob Owens and ribotyped at the Anaerobe Reference Laboratory (Cardiff, Wales, UK) by Dr Jon Brazier.

Triple-Stage Chemostat Human Gut Model

The gut model was designed to allow the study of the intestinal microflora in the low pH, carbohydrate-excess conditions of the proximal colon and the carbohydrate-depleted, non-acidic conditions of the distal colon (Macfarlane et al., *Microb Ecol* 1998; 35: 180-7). Microbiological and physicochemical measurements within the gut model vessels were validated against the intestinal contents of sudden death victims (Macfarlane et al., *Microb Ecol* 1998; 35: 180-7). Each gut model consists of three fermentation vessels connected in a weir cascade system top-fed with growth medium at a controlled rate (D=0.015 $h^{-1}$). Vessels were sparged with oxygen-free nitrogen to ensure anaerobiosis, heated via a water-jacketed system (37° C.) and maintained at specific pH using fermenter controller units (Biosolo 3, Brighton Systems, UK) delivering 0.5 M HCl/NaOH. Vessel 1 (280 mL) was operated at pH 5.5 and high substrate availability, thus reflecting the conditions within the proximal colon, while vessels 2 and 3 (300 mL) were operated at pH 6.2 and 6.8, respectively, with low substrate availability, thus reflecting the conditions within the distal colon. The gut model was primed with faecal slurry ~10% (w/v) and allowed to equilibrate with respect to bacterial populations for 14 days.

Preparation of the Gut Models

Faecal samples were collected from five healthy elderly (>65 years) volunteers and immediately transported to the laboratory under anaerobic conditions (GasPak, Oxoid, Basingstoke, UK). Stools were confirmed as *C. difficile* culture-negative on Brazier's CCEY agar incorporating 5 mg/L lysozyme (Sigma-Aldrich, UK) as reported previously (Baines et al., *J Antimicrob Chemother* 2005; 55: 974-82; Freeman et al., *J Antimicrob Chemother* 2003; 52: 96-102). *C. difficile*-negative faeces were pooled and a coarse-filtered slurry (~10% w/v) in sterile pre-reduced phosphate-buffered saline was prepared. Vessels of the gut models were filled to approximately two-thirds volume, and the growth medium pumps were started.

Enumeration of Gut Microflora and *C. difficile*

Major culturable components of the indigenous gut microflora and *C. difficile* were enumerated by viable counting ($log_{10}$ cfu/mL) on selective and non-selective agars as reported previously (Freeman et al., *J Antimicrob Chemother* 2005; 56: 717-25). Bacterial groups enumerated were: total facultative anaerobes, facultatively anaerobic lactose fermenters, total anaerobes, bifidobacteria, *Bacteroides fragilis* group, total clostridia, lactobacilli, enterococci, total *C. difficile* and *C. difficile* spores. *C. difficile* cytotoxin production was quantified using a Vero cell cytotoxicity assay as described previously (Freeman et al., *J Antimicrob Chemother* 2003; 52: 96-102). Cytotoxin titres were expressed in $log_{10}$ relative units (RU). Only *C. difficile* total bacterial counts, spore counts and cytotoxin titres were enumerated in vessel 1 of the gut model.

Gut Model Experimental Design

The use of the gut model to evaluate therapeutic interventions for CDI has been described previously (Freeman et al., *J Antimicrob Chemother* 2007; 60: 83-91; Freeman et al., *J Antimicrob Chemother* 2005; 56: 717-25). Briefly, following inoculation of each gut model with the faecal slurry, no further interventions were made for 13 days (period A). During period A, bacterial populations were enumerated every 2 days. Next (day 14), vessel 1 of each gut model was inoculated with a single inoculum of ~$10^7$ cfu *C. difficile* PCR ribotype 027 spores (Freeman et al., *J Antimicrob Chemother* 2003; 52: 96-102), with no further interventions for 7 days (period B). From this point onwards, bacterial populations were enumerated daily. A further single inoculum of *C. difficile* PCR ribotype 027 spores was instilled into vessel 1 of each gut model (day 21) in addition to 33.9 mg/L clindamycin (Pfizer, USA) four times daily for 7 days (period C). This instillation regimen aimed to maintain clindamycin levels within the gut model approximately equivalent to those observed in vivo following a single 600 mg dose (Brown et al., *Ann Intern Med* 1976; 84: 168-70). Following cessation of clindamycin instillation, no further interventions were made (period D) until high-level cytotoxin production (≥4 RU) was observed for at least 2 consecutive days. Installation of vancomycin (single experiment, 125 mg/L four times daily) and oritavancin (single experiment, 64 mg/L two times daily) was initiated on day 39 in each experiment for 7 days (period E). Vancomycin (Sigma-Aldrich) was prepared in distilled water and oritavancin (Targanta Therapeutics, Cambridge, USA) was prepared in 0.002% (v/v in distilled water) polysorbate-80 (Sigma-Aldrich) and both antimicrobial solutions were sterilized by filtration (0.22 um) prior to installation into the gut model. The vancomycin installation regimen aimed to achieve antibiotic concentrations reflective of those observed in vivo following a standard course of therapy in humans (Young et al., *Gastroenterology* 1985; 89: 1038-45). The antimicrobial installation regimen for oritavancin took into account the solubility limits of the drug in buffered culture media. Following cessation of therapeutic antimicrobial installation, bacterial populations and cytotoxin titres were followed for a further 15 days (period F).

Bioassay of Active Antibiotic Concentrations

Concentrations of clindamycin were not determined in the present studies. Vancomycin and oritavancin concentrations within the vessels of each gut model were determined using an in-house large plate bioassay. Briefly, samples (1 mL) from all vessels of each gut model were centrifuged (16,000 g) and stored at −20° C. prior to bioassay. One hundred milliliters of Muller-Hinton agar (Oxoid, UK) supplemented with 1 M para-amino benzoic acid was sterilized by autoclaving, cooled to 50° C. and inoculated with 1 mL of the indicator organism *Staphylococcus aureus* ATCC 29213 (at a turbidity equivalent to that of a 0.5 McFarland standard). Molten agar was transferred aseptically into 245 $mm^2$ Petri dishes (Fisher Scientific, Loughborough, UK) and allowed to set. The zone diameters were evaluated for differences with calibrators diluted in distilled water or sterile pH-adjusted (5.5, 6.2, 6.8) gut model fluid. As there was no appreciable difference in zone diameter in the different diluents, deionized water containing 0.002% polysorbate-80 was used for all oritavancin calibrators. Vancomycin calibrators were prepared in sterile deionized water. Samples from the gut model were sterilized by filtration (0.22 um). Twenty-five wells (9 mm diameter) were removed from the agar using a number 5 cork borer. Twenty microliters of each doubling dilution of vancomycin calibrator (1-512 mg/L), oritavancin calibrator (1-128 mg/L) or sample from the gut model was assigned randomly to each well in triplicate. Oritavancin was filtered at 1280 mg/L as filtration at lower concentrations leads to significant proportional losses of drug owing to saturable surface binding. Agar plates were refrigerated (4° C.) for 5 h to allow antimicrobial diffusion while minimizing bacterial growth, following which bioassay plates were incubated aerobically at 37° C. for 48 h. Zone diameters were measured using calipers accurate to 0.01 mm and calibration lines were produced by plotting diameter squared against $log_2$ concentration of antimicrobial. Unknown antimicrobial concentrations were read from the calibration line for each plate, and converted into actual concentrations using an inverse $log_2$ function. Mean antimicrobial concentrations (mg/L) were averaged from the three replicates. Limits of detection for oritavancin and vancomycin bioassays were 2 and 8 mg/L, respectively.

Results

Inter-experiment variations in viable counts of indigenous gut bacteria and *C. difficile* PCR ribotype 027 between vessels 2 and 3 were very small. Therefore, only the results from vessel 3 are presented. Meaningful differences in observations between vessels 2 and 3 of the gut models will be highlighted where appropriate. Viable counts of enumerated components of the indigenous gut microflora were stable throughout period A in both oritavancin (FIG. 8a) and vancomycin (FIG. 8b) experiments. Installation of *C. difficile* PCR ribotype 027 spores (day 14, period B) did not substantially affect viable counts of any enumerated components of the gut microflora in either experiment.

Effects of Clindamycin Exposure on Gut Microflora

Figure 8A:
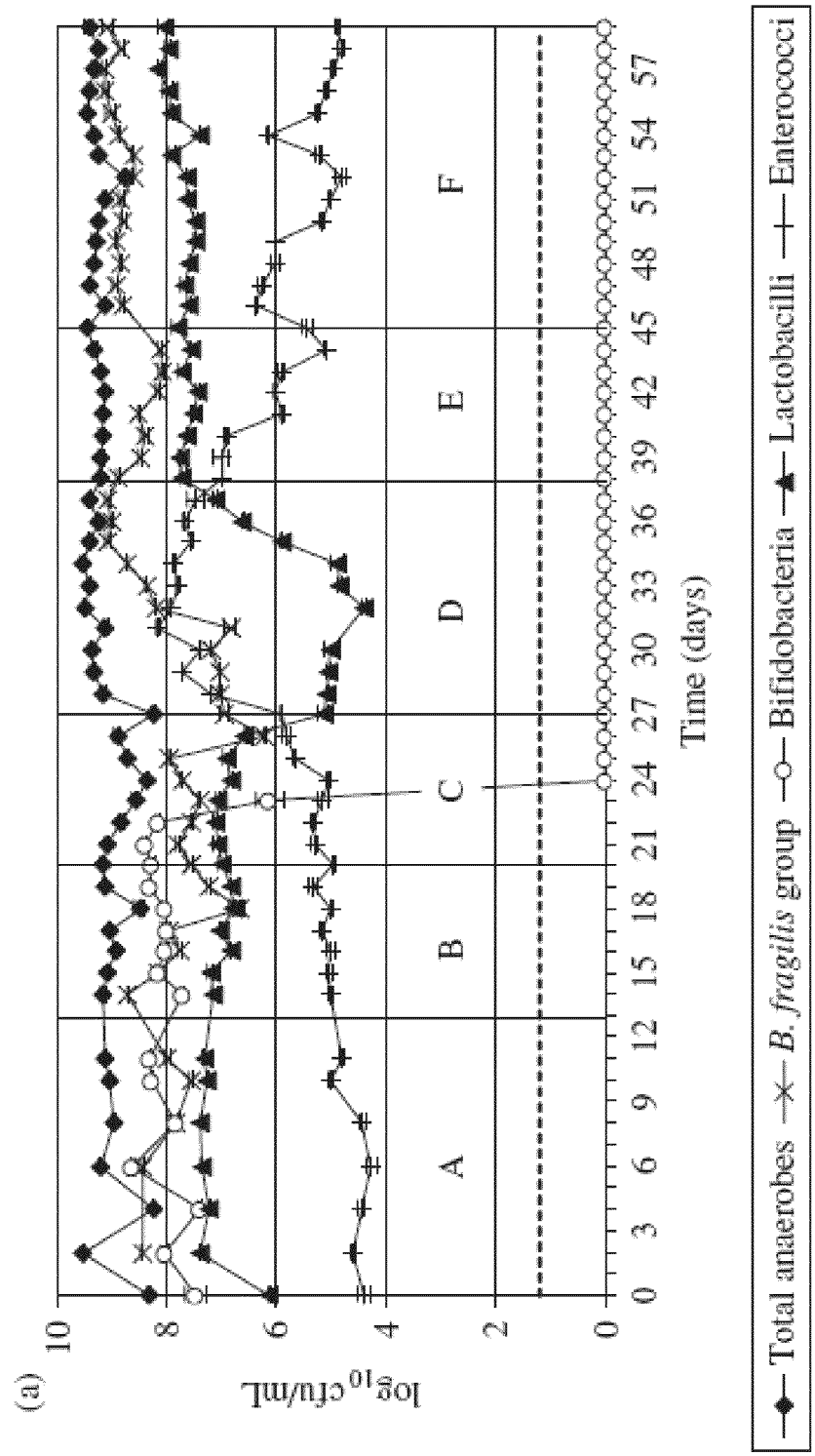
Figure 8B:
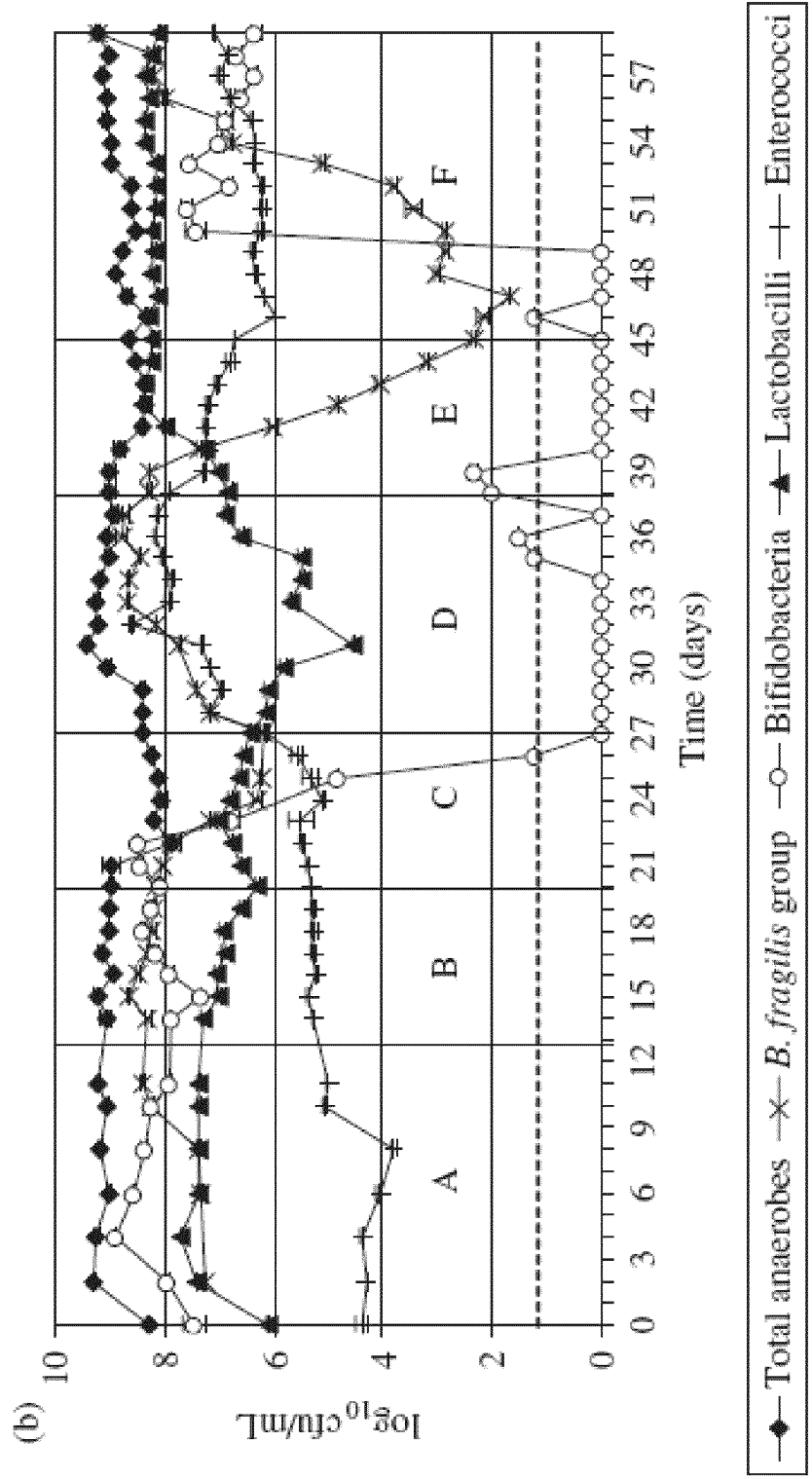

Installation of clindamycin (period C) elicited marked declines in populations of bifidobacteria (~6 $log_{10}$ cfu/mL), which were below the limits of detection (~2 $log_{10}$ cfu/mL) by the end of period C in both experiments (FIGS. 8a and b). Viable counts of *Bacteroides* and *lactobacilli* declined by ~1-2 $log_{10}$ cfu/mL in both experiments, while enterococcal viable counts increased by ~2 $log_{10}$ cfu/mL. Following cessation of clindamycin installation (period D), bifidobacterial populations remained below the limits of detection prior to installation of oritavancin and vancomycin. All other components of the indigenous gut microflora recovered to or exceeded their steady-state (period A) concentrations.

Effects of Oritavancin and Vancomycin Installation on Gut Microflora

Installation of oritavancin (period E) was followed by minor deleterious effects on the indigenous gut microflora that were enumerated. Bacteroides and enterococcal populations were the only bacterial groups adversely affected by oritavancin installation, declining by ~1 and 2 $log_{10}$ cfu/mL, respectively (FIG. 8a). Declines in *Bacteroides* and enterococcal populations following vancomycin installation were ~6 and 1 $log_{10}$ cfu/mL, respectively (FIG. 8b). *Bifidobacterial* populations remained below the limits of detection during period E in both experiments. Following cessation of oritavancin installation (period F), all bacterial populations recovered to steady-state (period A) concentrations, except bifidobacteria which remained below the limits of detection (FIG. 8a). Following cessation of vancomycin installation, all indigenous gut bacterial populations recovered to steady-state (period A) concentrations, except bifidobacteria, which were ~2 $log_{10}$ cfu/mL lower (FIG. 8b). *C. difficile* were not recovered during steady state (period A) in either experiment. In the absence of clindamycin installation (period B), *C. difficile* PCR ribotype 027 remained as spores in all vessels of the gut model (data for vessels 1 and 2 not shown) in both experiments (FIGS. 9a and b). *C. difficile* numbers declined by ~1 $log_{10}$ cfu/mL in vessel 3 and at a similar rate during period B in both experiments and cytotoxin production was not detected.

Effects of Clindamycin Exposure on *C. difficile*

Figure 9A:
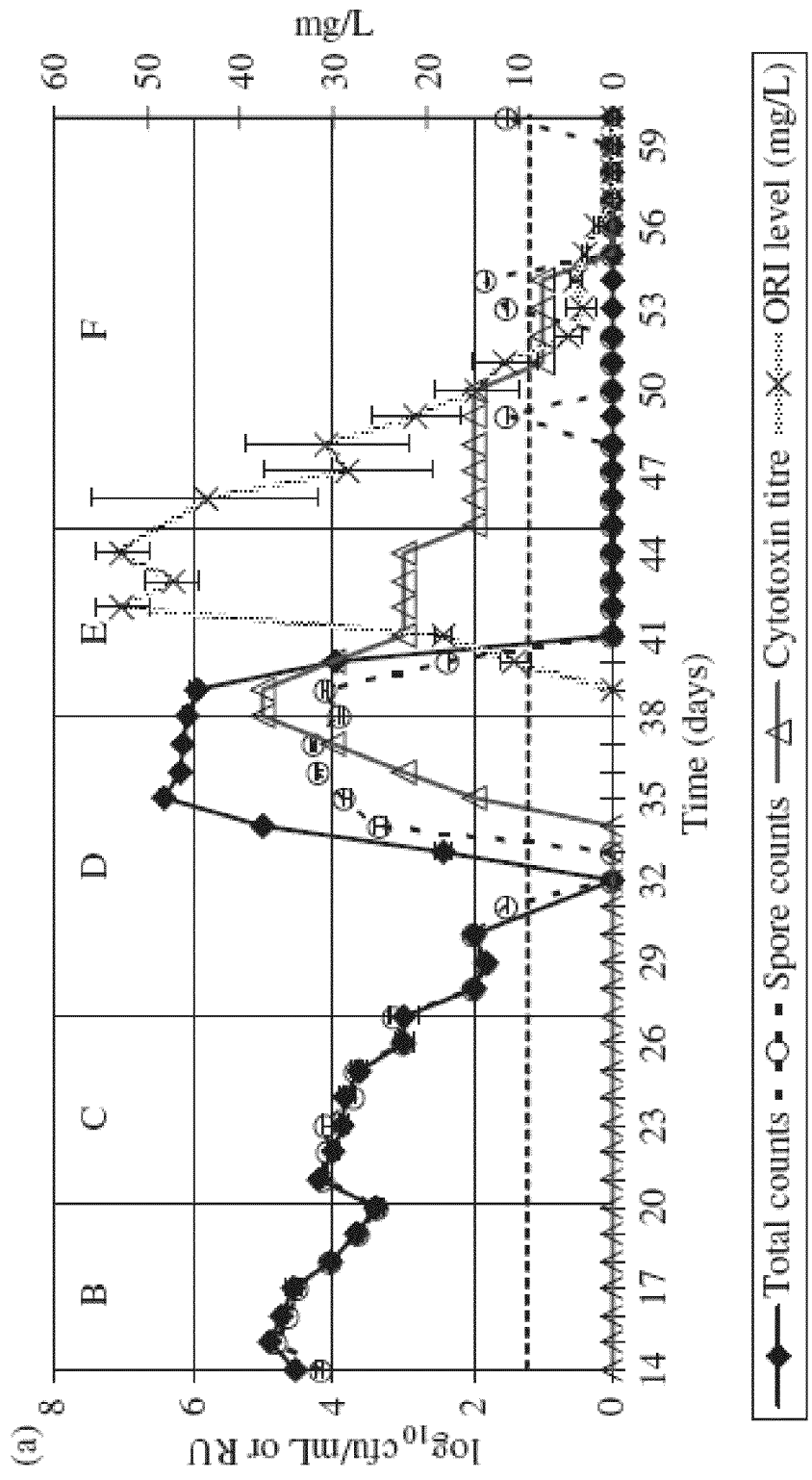
Figure 9B:
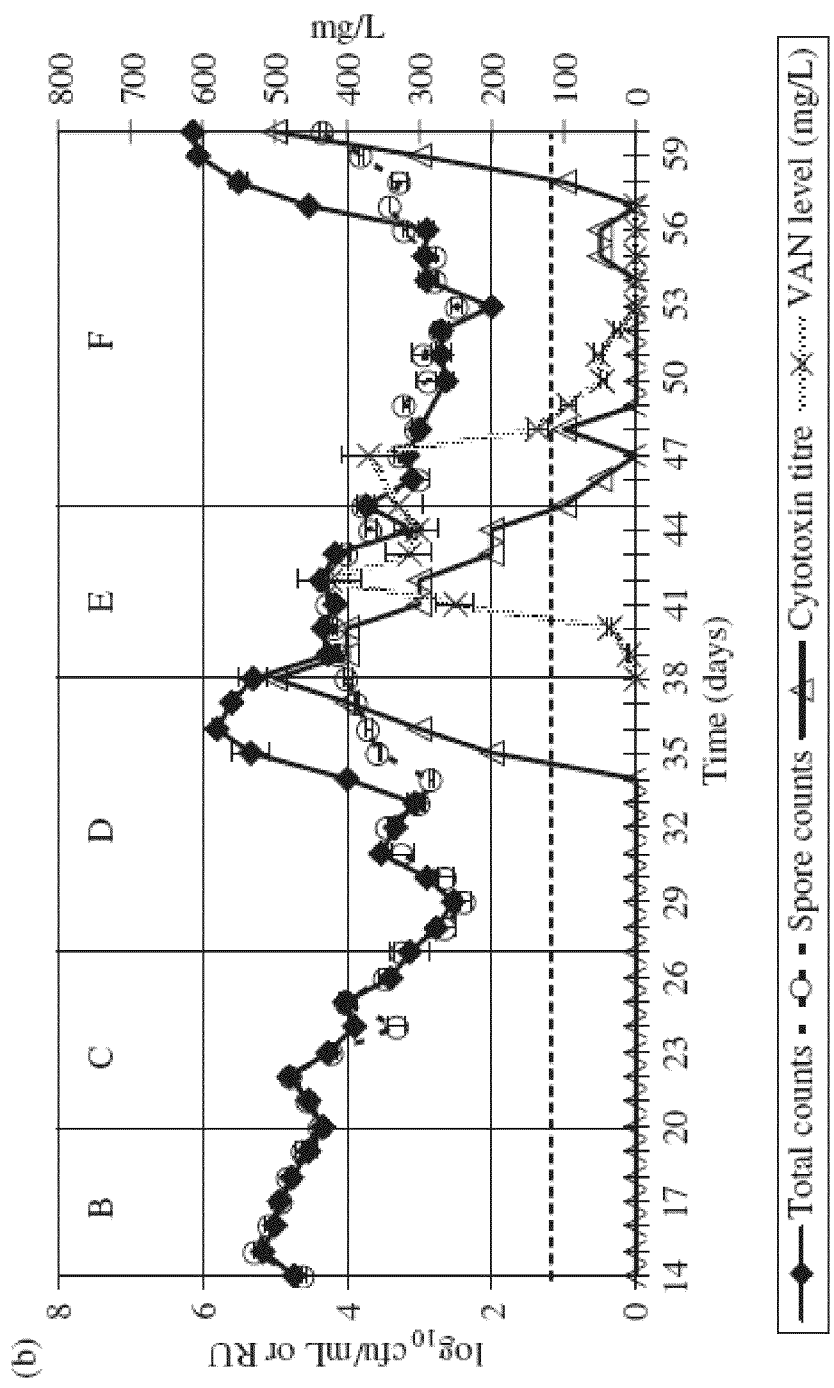

*C. difficile* remained as spores during clindamycin installation (period C) in both oritavancin and vancomycin experiments (FIGS. 9a and b). Additionally, cytotoxin production was not detected during this period. Following cessation of clindamycin installation (period D), *C. difficile* remained as spores, which were at the limits of detection 5 days after cessation of clindamycin installation in the oritavancin experiment (FIG. 9a). In the same period during the vancomycin experiment, *C. difficile* spore numbers declined for the first 2 days of period D, following which *C. difficile* spore numbers increased by ~1 $log_{10}$ cfu/mL (FIG. 9b). Germination of *C. difficile* spores was detected 6 and 7 days after cessation of clindamycin installation in oritavancin and vancomycin experiments, respectively. Vegetative *C. difficile* numbers increased sharply to peak viable counts of ~6 $log_{10}$ cfu/mL in both experiments. Cytotoxin production was detected on day 35 in both experiments and reached maximal titres of 5 RU in both experiments. Installation of treatment antimicrobial agents commenced on day 39 in both experiments. *C. difficile* spore germination, proliferation and high-level cytotoxin production were not observed in vessel 1 of the gut model in either oritavancin or vancomycin experiments during period D (data not shown).

Effects of Oritavancin Instillation on *C. difficile*

*C. difficile* total counts were ~2 $\log_{10}$ cfu/mL above spore counts (6 $\log_{10}$ cfu/mL) when instillation of oritavancin commenced (period E, FIG. 9a). On day 2 of oritavancin instillation, both *C. difficile* total counts and spore counts declined by ~2 $\log_{10}$ cfu/mL and were below the limits of detection (~1.22 $\log_{10}$ cfu/mL) 1 day later, remaining so for the rest of period E. Cytotoxin titres declined by 3RU during oritavancin instillation (period E). Oritavancin concentrations peaked at 128, 109 and 52 mg/L in vessels 1, 2 and 3, respectively, i.e. ~8-fold lower than those achieved in the vancomycin gut model. It is possible that the concentration of oritavancin demonstrated in culture samples from the gut model may be under-represented due to potential loss following filtration as concentrations were <1280 mg/L. All calibration line $R^2$ values were >0.95.

Effects of Vancomycin Instillation on *C. difficile*

*C. difficile* total counts declined by ~1.5 $\log_{10}$ cfu/mL after 1 day of vancomycin instillation (period E, FIG. 9b). *C. difficile* spore counts were unaffected by vancomycin instillation and *C. difficile* remained predominantly as spores for the remainder of period E. Cytotoxin titres declined by 3 RU during vancomycin instillation. Vancomycin concentrations peaked at 957, 800 and 423 mg/L in vessels 1, 2 and 3 of the gut model, respectively. All calibration line $R^2$ values were >0.99.

Events Following Cessation of Oritavancin Instillation

*C. difficile* was isolated sporadically at the limits of detection for the remainder of the experiment (period F, FIG. 9a). Centrifugation and washing of culture samples, in addition to exposure to activated charcoal (20-40 g/L) in an effort to minimize oritavancin carry-over, did not enhance the recovery of *C. difficile* (data not shown). Cytotoxin titres continued to decline and were below the limits of detection within 10 days. Oritavancin concentrations were below the limits of detection 11 days after cessation of oritavancin instillation.

Events Following Cessation of Vancomycin Instillation

*C. difficile* remained as spores until 12 and 13 days after cessation of vancomycin instillation in vessels 2 (data not shown) and 3, respectively (period F, FIG. 9b), following which recurrent germination, proliferation and high-level cytotoxin production were observed. *C. difficile* total counts were ~6 $\log_{10}$ cfu/mL and cytotoxin titres were 5 RU by the end of the experiment.

These results demonstrate that both oritavancin and vancomycin were effective in inhibiting vegetative *C. difficile*. Vancomycin instillation facilitated the inhibition of vegetative *C. difficile* such that only *C. difficile* spores remained in the vessels of the gut model 1 day after the start of vancomycin instillation. *C. difficile* spores were unaffected by the presence of vancomycin concentrations that were >500-fold above the MIC for vegetative forms of *C. difficile* PCR ribotype 027 (O'Connor et al., *J Antimicrob Chemother* 2008; doi:10.1093/jac/dkn276). The failure of vancomycin to elicit inhibitory activity against *C. difficile* spores at concentrations observed in faeces has been reported previously and supports the data presented in this study (Freeman et al., *J Antimicrob Chemother* 2005; 56: 717-25; Levett, *J Antimicrob Chemother* 1991; 27:55-62; Walters et al., *Gut* 1983; 24: 206-12). Additionally, following a decline in vancomycin concentrations below the limits of detection in vessels 2 and 3 of the gut model during period F, a further episode of *C. difficile* spore germination, proliferation and high-level cytotoxin production was observed.

Oritavancin rapidly reduced the numbers of both vegetative and spore forms of *C. difficile*, despite active peak antimicrobial concentrations ~8-fold lower than vancomycin. These active concentrations of oritavancin were 25- and 200-fold greater than the MIC for *C. difficile* PCR ribotype 027 when measured by agar incorporation and broth macrodilution methods, respectively (O'Connor et al., *J Antimicrob Chemother* 2008; doi:10.1093/jac/dkn276). Despite efforts to remove active oritavancin from culture samples by washing and charcoal adsorption, *C. difficile* could not be recovered other than sporadically isolated individual colonies at the limits of detection. Therefore, a marked difference in the effect of oritavancin against *C. difficile* spores was observed in the present studies in comparison with vancomycin. Indeed, it was recently observed that inhibition of outgrowth of *C. difficile* PCR ribotype 027 spores exposed to oritavancin (10 mg/L) persisted after the drug was removed by washing, this effect not being observed for either metronidazole- or vancomycin-exposed spores. No antimicrobial agent tested demonstrated any inhibitory activity against spore germination at supra-MIC concentrations; therefore, oritavancin appears to possess activity against *C. difficile* spore outgrowth. No recrudescence of *C. difficile* spore germination, proliferation and high-level cytotoxin production was observed in the present study during period F following oritavancin instillation, in direct contrast to vancomycin, even after antimicrobial concentrations declined below the limits of detection.

Oritavancin has been demonstrated previously to bind to surfaces, an effect abrogated by 0.002% polysorbate-80 (Arhin et al., *Antimicrob Agents Chemother* 2008; 52:1597-603). Polysorbate-80 was incorporated in the gut model growth medium (0.2% v/v), and thus binding to surfaces within the gut model with resultant continued antimicrobial activity below the limits of bioassay detection is an unlikely explanation for the failure to isolate *C. difficile* spores for large parts of period F in the present study. Although the decline in *C. difficile* cytotoxin titres was similar during period E (3 RU) in both oritavancin and vancomycin experiments, it took longer (5 days) for cytotoxin titres to decline to undetectable levels in the oritavancin experiment.

In conclusion, both oritavancin and vancomycin effectively eliminated vegetative *C. difficile* from the gut model, but only oritavancin demonstrated potential activity against spores. Recrudescence of *C. difficile* PCR ribotype 027 spores was observed following the decline in antibiotic levels to below the limits of detection for vancomycin, but this phenomenon was not seen for oritavancin. These findings suggest that oritavancin may have a therapeutic advantage over vancomycin in terms of anti-spore activity.

Example 5

Evaluating Efficacy of Intravenous Administration of Oritavancin in Hamster Model of CDI Methods
Bacterial Strain

*C. difficile* ATCC 43255 was used in all experiments. This strain was originally isolated from an abdominal wound and is toxin A+/B+ and binary toxin negative. *C. difficile* spores were prepared for the infection by incubating *C. difficile* cells on blood agar plate at 37° C. anaerobically for 7 days, to promote spore formation. The *C. difficile* colonies were resuspended in phosphate buffered saline (PBS) and mixed with an equal volume of 100% ethanol for one hour. The spores were centrifuged, resuspended in PBS, aliquoted, and frozen at −20° C. Spores were diluted in PBS for oral inoculation into hamsters.

Hamster Model of *C. difficile* Infection (CDI)

All studies were performed in accordance with protocols that were approved by the Institutional Animal Care and Use Committee. Male Syrian golden hamsters (65-80 g; Harlan, Indianapolis, Ind.) were pre-treated with a single subcutaneous dose of clindamycin (100 mg/kg) one day prior to the infection (Day −1). One day later (Day 0), animals were infected orally with $10^5$ *C. difficile* spores by oral gavage.

Antibiotherapy

Starting on Day 1 post-infection, either vehicle, vancomycin (50 mg/kg), or oritavancin formulated in 10% hydroxypropyl β-cyclodextrin (HPCD) (50 mg/kg) was administered intravenously (sublingual) to the hamsters (n=10/group). A total of either 1, 2 or 3 doses of oritavancin was injected on Days 1, 3, and 5, respectively (q2d). In the comparator group, the hamsters received a total of 3 doses of vancomycin administered on Days 1, 3, and 5 Animals were observed for any signs of disease until the experimental endpoint and survival was recorded.

Results

CDI was induced in hamsters (n=10/group) by priming with clindamycin on day −1 and thereafter infecting with *C. difficile* 24 h later (Day 0). The infected hamsters received the first dose of antibiotic on day 1 and treatment was repeated each 2 days for up to five days; an untreated group was used as control.

All untreated animals developed CDI as assessed by clinical signs and either died or were euthanized in a moribund state by day 5 (FIG. 10). Three intravenous doses of 50 mg/kg q2d of vancomycin prolonged the survival by 8 days compared to untreated animals (FIG. 10). However, 70% of the vancomycin-treated animals died between the second and the third injections on Days 3 and 5, respectively. As a result, on Day 5 proportional survival rates were 0% for untreated animals and 30% for vancomycin-treated animals. In contrast, animals receiving oritavancin intravenously at 50 mg/kg once, twice or thrice q2d for 5 days exhibited increased proportional survival relative to untreated animals, with survival prolonged by 4, 5 and 7 days more than untreated animals, respectively (FIG. 10). This finding indicated dose-dependent efficacy of oritavancin Animals that received 2 doses of oritavancin survived 5 days longer than those having received equivalent dose and dose regimen (2×q2d) with vancomycin (FIG. 10).

Example 6

Evaluating Efficacy of Oral Administration of Oritavancin in Hamster Model of CDI Methods Bacterial Strain

*C. difficile* (CD) ATCC 43255 was used in all experiments. CD spores were prepared for the infection by incubating CD cells on blood agar plate at 37° C. anaerobically for 7 days, to promote spore formation. The CD colonies were resuspended in phosphate buffered saline (PBS) and mixed with an equal volume of 100% ethanol for one hour. The spores were centrifuged, resuspended in PBS, aliquoted, and frozen at −20° C. Spores were diluted in PBS for oral inoculation into hamsters.

Hamster Model of CD Infection (CDI)

All studies were performed in accordance with protocols that were approved by the Institutional Animal Care and Use Committee. Male Syrian golden hamsters (65-80 g) were pre-treated with a single subcutaneous dose of clindamycin (CL) (100 mg/kg) one day prior to the infection (Day −1). One day later (Day 0), animals were infected orally with 105 CD spores.

Antibiotherapy

1) Starting on Day 1 post-infection (PI), a single dose of either vehicle, vancomycin (VA) (50 mg/kg/day), or oritavancin (ORI) formulated in 10% hydroxypropyl β-cyclodextrin (HPCD) (10, 50 or 100 mg/kg/day) was administered to the hamsters (n=10/group) by gavage for 5 days. 2) ORI formulated in polyethylene glycol 400 (PEG400) was given orally to hamsters (n=5/group) on Day 2 for 5 days Animals were observed for any signs of disease until the experimental endpoint (Day 20) and survival was recorded.

Detection of CD in Caecal Contents

Detection of CD cells and toxins were detected in the caecal contents of animals at both the experimental and clinical endpoints. Presence of CD toxins (toxin A and B) were detected by using the CD TOX A/B IITM kit (Techlab) as described by the manufacturer. Limit of detection was ≥0.8 ng/mL for Toxin A and ≥2.5 ng/mL of Toxin B. Total viable cells (TC) (both vegetative and spore forms) were enumerated by serially diluting the caecal content by 10 fold in PBS containing 2% oxyrase (Oxyrase Inc). The caecal content dilutions were plated on Brazier's CCEY lysozyme agar (Lab160) without egg yolk. CD spores were counted by treating caecum samples with an equal volume of pure ethanol. The limit of detection (LOD) was 1.47 and 1.77 Log 10 CFU/g caecal content for TC and spores, respectively.

Statistical Analyses

Data were analyzed by Kaplan-Meier and Log rank Wilcoxon tests survival analysis by using GraphPad Prism (version 5.00). A p-value lower than 0.05 (p<0.05) was considered to indicate statistical significance.

Results

As shown graphically in FIG. 11A after treatment with CL alone, only 50% of hamsters survived to day 20, with all deaths occurring between Days 6-8 PI. Challenge of CL-primed hamsters with CD spores led to 0% survival at Day 4 PI.

As shown graphically in FIG. 11B, the efficacy of ORI was dose-dependent. ORI injected at 10, 50 and 100 mg/kg once daily (formulated in HPCD) for 5 days prolonged survival by 9, 13 and ≥17 days more than untreated animals, respectively (p<0.0001, for each group). ORI at 100 mg/kg exhibited superior efficacy to VA on Day 12 PI. The mean survival time of hamsters treated with ORI 100 mg/kg was 17 days compared to 12 days for those treated with VA (p<0.0001). Caecal contents from all dead hamsters were positive for CD Toxin A and B.

Shown graphically in FIG. 11C are the results of oral treatments started on Day 1 or Day 2 for 5 days with VA 50 mg/kg once daily or ORI 100 mg/kg once daily, respectively. All the animals treated with ORI survived and none of them showed any sign of disease up to 20 days PI. High level of toxin A and B were detected in caecal contents of the untreated and VA-treated animals, while toxins A and B were undetectable in caecal content of animals treated with ORI on Day 20 PI.

As shown in FIG. 11D, at 20 days PI, CD vegetative and spore cells were undetectable in the caecal content of all hamsters treated with ORI formulated in PEG400. LOD, limit of detection was 1.47 and 1.77 Log 10 CFU/g caecal content for TC and spores, respectively.

The invention of this application has been described above both generically and with regard to specific embodiments.

Although the invention has been set forth in what is believed to be the preferred embodiments, a wide variety of alternatives known to those of skill in the art can be selected within the generic disclosure. The invention is not otherwise limited, except for in the recitation of the claims.

All documents, publications, patents, books, manuals, articles, papers, abstracts, posters and other materials referenced herein are expressly incorporated herein by reference in their entireties.

We claim:

1. A method of treating a *C. difficile* infection in a subject, consisting of administering a therapeutically effective amount of a glycopeptide antibiotic to a subject having a *C. difficile* infection, thereby treating a *C. difficile* infection in a subject, wherein the glycopeptide antibiotic is oritavancin, or a pharmaceutically acceptable salt, hydrate, or solvate thereof, or a mixture thereof.

2. The method of claim 1, wherein *C. difficile* is a vegetative form of *C. difficile*, a *C. difficile* spore or a mixture of both.

3. The method of claim 1, wherein the glycopeptide antibiotic is in the form of a pharmaceutical composition comprising the glycopeptide antibiotic and a pharmaceutically acceptable carrier or diluent.

4. The method of claim 1, wherein said treating inhibits outgrowth of a *C. difficile* spore, inhibits growth of a vegetative form of *C. difficile* or inhibits *C. difficile* sporulation.

5. The method of claim 1, wherein the therapeutically effective amount of the glycopeptide antibiotic is between about 5 and 30 mg/kg body weight.

6. The method of claim 1, wherein said administering is BID for four days.

7. A method of preventing a *C. difficile* infection in a subject, consisting of administering to a subject exposed to *C. difficile* bacteria an amount of a glycopeptide antibiotic sufficient to prevent *C. difficile* infection, thereby preventing a *C. difficile* infection in a subject, wherein the glycopeptide antibiotic is oritavancin, or a pharmaceutically acceptable salt, hydrate, or solvate thereof, or a mixture thereof.

8. The method of claim 7, wherein *C. difficile* is a vegetative form of *C. difficile*, a *C. difficile* spore or a mixture of both.

9. The method of claim 7, wherein said administering is via intravenous administration or oral administration.

10. The method of claim 7, wherein the glycopeptide antibiotic is in the form of a pharmaceutical composition comprising the glycopeptide antibiotic and a pharmaceutically acceptable carrier or diluent.

11. The method of claim 7, wherein said preventing inhibits outgrowth of a *C. difficile* spore, inhibits growth of a vegetative form of *C. difficile* or inhibits *C. difficile* sporulation.

12. The method of claim 7, wherein the amount of a glycopeptide antibiotic sufficient to prevent *C. difficile* infection is between about 5 and 30 mg/kg body weight.

13. The method of claim 7, wherein said administering is BID for four days.

* * * * *